(12) United States Patent
Williams et al.

(10) Patent No.: US 7,029,838 B2
(45) Date of Patent: Apr. 18, 2006

(54) PREVASCULARIZED CONTRUCTS FOR IMPLANTATION TO PROVIDE BLOOD PERFUSION

(75) Inventors: Stuart K. Williams, Tucson, AZ (US); James B. Hoying, Tucson, AZ (US); Benjamin R. Shepherd, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 10/112,461

(22) Filed: Mar. 29, 2002

(65) Prior Publication Data

US 2002/0142458 A1    Oct. 3, 2002

Related U.S. Application Data

(60) Provisional application No. 60/279,824, filed on Mar. 30, 2001.

(51) Int. Cl.
*A01N 1/00* (2006.01)
*A01N 65/00* (2006.01)
*C12N 5/02* (2006.01)
*C12N 5/00* (2006.01)

(52) U.S. Cl. .................. 435/1.1; 424/93.1; 435/325; 435/395

(58) Field of Classification Search ............... 435/325; 424/93.1
See application file for complete search history.

(56) References Cited

U.S. PATENT DOCUMENTS

| | | | |
|---|---|---|---|
| 3,949,073 A | 4/1976 | Daniels et al. ............... 424/177 |
| 4,963,489 A | 10/1990 | Naughton et al. ........ 435/240.1 |
| 5,131,907 A * | 7/1992 | Williams et al. ............... 600/36 |
| 5,266,480 A | 11/1993 | Naughton et al. .... 435/240.243 |
| 5,510,254 A | 4/1996 | Naughton et al. .... 435/240.243 |
| 5,512,475 A | 4/1996 | Naughton et al. .... 435/240.243 |
| 5,516,680 A | 5/1996 | Naughton et al. .... 435/240.243 |
| 5,516,681 A | 5/1996 | Naughton et al. .... 435/240.243 |
| 5,518,915 A | 5/1996 | Naughton et al. .... 435/240.243 |
| 5,541,107 A | 7/1996 | Naughton et al. .... 435/240.243 |
| 5,559,022 A | 9/1996 | Naughton et al. ........ 435/240.2 |
| 5,578,485 A | 11/1996 | Naughton et al. .... 435/240.243 |
| 5,624,840 A | 4/1997 | Naughton et al. .......... 435/395 |
| 5,628,781 A | 5/1997 | Williams et al. ................ 623/1 |
| 5,672,346 A | 9/1997 | Srour et al. ..................... 435/2 |
| 5,709,854 A | 1/1998 | Griffith-Cima et al. ... 424/937.7 |
| 5,763,267 A | 6/1998 | Kurjan et al. ............. 435/293.1 |
| 5,785,964 A | 7/1998 | Naughton et al. ........ 424/93.21 |
| 5,792,603 A | 8/1998 | Dunkelman et al. .......... 435/1.2 |
| 5,827,735 A | 10/1998 | Young et al. ................. 435/325 |
| 5,842,477 A | 12/1998 | Naughton et al. ........... 128/898 |
| 5,846,828 A * | 12/1998 | Peterson et al. ............. 435/399 |
| 5,858,721 A | 1/1999 | Naughton et al. .......... 435/69.1 |
| 5,863,531 A | 1/1999 | Naughton et al. .......... 424/93.7 |
| 5,902,741 A | 5/1999 | Purchio et al. ......... 435/240.23 |
| 5,957,972 A | 9/1999 | Williams et al. ................. 623/1 |
| 5,962,325 A | 10/1999 | Naughton et al. ........... 435/395 |
| 6,022,743 A | 2/2000 | Naughton et al. ........... 435/395 |
| 6,060,306 A | 5/2000 | Flatt et al. ................. 435/297.2 |
| 6,121,042 A | 9/2000 | Peterson et al. .......... 435/284.1 |
| 6,218,182 B1 | 4/2001 | Naughton et al. ........... 435/395 |
| 6,224,893 B1 | 5/2001 | Langer et al. ............... 424/423 |

OTHER PUBLICATIONS

Game et al, Wien Klin Wochenschr 2001;113:823-38.*
Alberto et al, Heart Surg Forum 2000;4:179-83.*
Robb, Seminars in Surg Oncol Oct. 2000;209-10.*
Kramer et al, Radiol 2000;216:123-7.*
Construct: Merriam-Webster's Online Dictionary, 2005.*
Bouhadir et al, J Drug Target. 2001;9(6):397-406.*
Nakano et al, Euro Surg Res 1999;31:240-8.*
Marler et al, Adv Drug Deliv Rev. Aug. 3, 1998;33(1-2): 165-182.*
Hoying et al, In Vitro Cell Dev Biol-Animal 1996;32:409-19.*
Hoying et al., "Effects of Basic Fibroblast Growth Factor on Human Microvessel Endothelial Cell Migration on Collagen I Correlates Inversely with Adhesion and is Cell Density Dependent," J. Cell. Physio. 168:294-304,1996.
Yancopoulos et al., "Vascular-Specific Growth Factors and Blood Vessel Formation," Nature, vol. 407, Sep. 14, 2000.
Kuzuya et al., "Reorganization of Endothelial Cord-Like Structures on Basement Membrane Complex (Matrigel) : Involvement of Transforming Growth Factor β1," J. Cell. Physio. 161:267-276 (1994).

(Continued)

*Primary Examiner*—Q. Janice Li
(74) *Attorney, Agent, or Firm*—Gavin J. Milczarek-Desai; Quarles & Brady Streich Lang, LLP

(57) ABSTRACT

This application discloses methods and materials for preparing functional microvascular beds in the laboratory. These prevascularized constructs can be used to vascularize engineered tissue constructs or to revascularize damaged or diseased tissues or organs following implantation. The prevascularized constructs may also deliver genetically engineered gene products to the bloodstream.

7 Claims, 9 Drawing Sheets

OTHER PUBLICATIONS

Young et al., "A Porcine Model for Adipose Tissue-Derived Endothelial Cell Transplantation," Cell Transplantation, vol. 1, pp. 293-298 (1992).

Hoying et al., "Angiogenic Potential of Microvessel Fragments Established in Three-Dimensional Collagen Gels," In Vitro 32:409-419, 1996.

Williams, Stuart, "Editorial: Angiogenesis in Three-Dimensional Cultures," Laboratory Investigation, vol. 69, No. 5, p. 491 (1993).

Schechner et al., "In vivo Formation of Complex Microvessels Lined by Human Endothelial Cells in an Immunodeficient Mouse," PNAS 97:9191-9196, 2000.

Zuk et al., "Multilineage Cells from Human Adipose Tissue: Implications for Cell-Based Therapies," Tissue Engineering, 7:211-228, 2001.

Richardson et al., "Polymeric System for Dual Growth Factor Delivery," Nat. Biotechnol. 19:1029-34, 2001.

Goto et al., "Synergistic Effects of Vascular Endothelial Growth Factor and Basic Fibroblast Growth Factor on the Proliferation and Cord Formation of Bovine Capillary Endothelial Cells within Collagen Gels," Laboratory Investigation, vol. 69, No. 5, p. 508-517 (1993).

Nicosia et al., "Growth of Microvessels in Serum-Free Matrix Culture of Rat Aorta," Laboratory Investigation vol. 63, No. 1, p. 115-22 (1990).

Hoying et al., "Rapid Perfusion of a Prevascularized Tissue Construct Following Implantation," ISACB vol. 11(1), p. 47 (2002).

Shepherd et al., Photomicrographs of Microvascular Construct, ISACB vol. 11(1), p. 59 (2002).

Lawley TJ and Kubato Y J. Invest Derm. 93:59s-61s 1989.

Nor JE et al., Lab Invest. 81:453-463 2001; Schechner JS et al. PNAS 97:9191-9196, 2000.

"Principles of Tissue Engineering, 2d ed.", Lanza, Langer, and Vacanti, eds., Academic Press, 2000.

"Methods of Tissue Engineering", Atala and Lanza, eds., Academic Press, 2001.

Animal Cell Culture, Masters, ed., Oxford University Press, 2000.

Middleton et al., Biomaterials 21:2335-2346, 2000.

Middleton et al., Medical Plastics and Biomaterials, Mar./Apr. 1998, at pp. 30-37.

Handbook of Biodegradable Polymers, Domb, Kost, and Domb, eds., 1997, Harwood Academic Publishers, Australia.

Rogalla, Minim. Invasive surg. Nurs. 11:67-69, 1997.

Klein, Facial Plast. Surg. Clin. North Amer. 9:205-18, 2001.

Klein et al., J. Dermatol. surg. Oncol. 11:337-39, 1985.

Frey et al., J. Urol. 154:812-15, 1995.

Peters et al., J. Biomed. Mater. Res. 43:422-27, 1998.

Kuijpers et al., J. Biomed. Mater. Res. 51:136-45, 2000.

Ausubel et al., Current Protocols in Molecular Biology (including supplements through Mar. 2002) John Wiley & Sons, New York, NY.

Sambrook et al., Molecular Cloning: A Laboratory Manual, 2nd Ed., Cold Spring Harbor Laboratory Press, Cold Spring Harbor, NY, 1989.

Sambrook and Russell, Molecular Cloning: A Laboratory Manual, 3rd Ed., Cold Spring Harbor Laboratory Press, Cold Spring Harbor, NY, 2001.

Beaucage et al., Current Protocols in Nucleic Acid Chemistry, John Wiley & Sons, New York, NY, 2000 (including supplements through Mar. 2002).

Short Protocols in Molecular Biology, 4th Ed., Ausbel, Brent, and Moore, eds., John Wiley & Sons, New York, NY, 1999.

Davis et al., Basic Methods in Molecular Biology, McGraw Hill Professional Publishing, 1995.

Embryonic Stem Cells, Methods and Protocols, Turksen, ed., Humana Press, 2002.

Weisman et al., Annu. Rev. Cell. Dev. Biol. 17:387-403.

Pittinger et al., Science, 284:143-47, 1999.

Jackson et al., PNAS 96(25) :14482-86, 1999.

Atola et al., particularly Chapters 33-41.

Prockop, Science, 276:71-74, 1997.

Theise et al., Hepatology, 31:235-40, 2000.

Current Protocols in Cell Biology, Bonifacino et al., eds., John Wiley & Sons, 2000 (including updates through Mar., 2002).

Atala et al., particularly Chapters 9-32.

Freshney, Culture of Animal Cells A Manual of Basic Techniques, 4th ed., Wiley Liss, John Wiley & Sons, 2000.

Basic Cell Culture: A Practical Approach, Davis, ed., Oxford University Press, 2002.

Animal Cell Culture: A Practical Approach, Masters, ed., 2000.

Atkins et al., J. of Heart and Lung Transplantation, Dec. 1999, at pp. 1173-1180.

Tomita et al., Cardiovascular Research Institute, American Heart Association, 1999, at pp. 92-101.

Sakai et al., Cardiovascular Research Institute, American Heart Association, 1999, at pp. 108-114.

Carter et al., Surgery, 120:1089-94, 1996.

London et al., Diabetes & Metabolism, 23:200-07, 1998.

Arita et al., Pancreas 23:62-67, 2001.

Essers et al., Cytogenet. Cell, Genet. 69:246-252, 1995.

Hauner et al., J. Clin. Endocrinol. Metabol. 64:832, 1987.

Katz et al., Clin. Plast. Surg. 26:587, 1999.

Liechty et al., Nature Medicine 6(11):1282-1286, 2000.

Stopeck et al., Cell Transplant. 6:1-8, 1997.

Jarrell et al., J. Vasc. Surg. 1:757-64, 1984.

Twyman, Advanced Molecular Biology: A Concise Reference, Bios Scientific Publishers, Springer Verlag New York, particularly Chapter 24.

Arita et al., Transplantation 68(5):705-07, 1999.

London et al., in Methods in Cell Transplantation, Ricordi, ed., at pp. 439-454, 1995.

Lakey et al., Transplantation 72:562-63, 2001.

Olack et al., Human Immunol. 60:1303-09, 1999.

London et al., Diabetes Metab. 24:200-07, 1998.

Linetsky et al., Diabetes 46:1120-23, 1997.

Wang et al., Nat. Biotechnol. 15:358-62, 1997.

Macdonald et al. in Atala et al., Chapter 11, particularly at pp. 155-166.

Williams et al., J. Surg. Res. 38:618-29, 1985.

Rupnick et al., J. Vascular Res. 9:788-95, 1989.

* cited by examiner

PREVASCULARIZED CONTRUCTS FOR IMPLANTATION TO PROVIDE BLOOD PERFUSION

RELATED APPLICATION INFORMATION

This application claims the filing date benefit of U.S. Provisional Patent Application Serial No. 60/279,824, filed Mar. 30, 2001, which is incorporated by reference in its entirety for any purpose.

DESCRIPTION OF THE INVENTION

1. Field of the Invention

The invention is directed generally to methods for vascularizing or revascularizing tissues and organs, including but not limited to donated tissues and organs, diseased or dysfunctional tissues and organs, and engineered tissues. Prevascularized constructs comprising microvessel fragments in a three dimensional culture, for use according to these methods, are also disclosed. Prevascularized constructs comprising genetically engineered cells for delivering a gene(s) or gene product(s) to an animal or human are also provided.

2. Background of the Invention

Transplants of cells and tissue engineered organs and tissues offer promise in facilitating tissue healing and repair and the replacement or treatment of diseased or dysfunctional organs. A primary challenge in the transplantation of tissue engineered constructs is ensuring sufficient blood supply to the constituent cells. In the absence of pre-existing vessels in the transplant capable of inosculation with the recipient blood supply, the amount of tissue that can be transplanted is limited by oxygen diffusion.

Ultimately, healthy transplants depend on sufficient vessel density within the transplanted tissue or organ and the organization of the vessels into a network comprised of low-resistance conduit vessels (arteries), a functional microcirculation (arterioles and capillaries) for a proper blood-tissue exchange, and drainage/compliance vessels (venules and veins). Thus, in certain respects, the extent to which tissue engineered constructs can be vascularized determines the limits of construct size and architecture. Consequently, techniques to provide rapid vascularization and perfusion of tissue engineered constructs should be incorporated into the tissue or organ design.

The ability to include a vascular network within an engineered tissue and engineer it to match a particular tissue represents a significant stride in the tissue engineering and artificial organ fields. A recent article in the "Red Herring", a leading technology layman's journal, described the prevascularization of an engineered organ to be the remaining, but most difficult, step in successfully growing organs in the laboratory.

Current tissue engineering strategies are hampered by the inability to pre-build a vasculature into the tissue. Any implanted tissue, engineered or donated, requires a blood supply in order to support the health and function of the tissue cells. In the case of most built or engineered tissues (tissue engineering), there is no vasculature within the construct to perform this function.

Existing strategies for building a vascular system for tissue engineered constructs have been based on using cultured, human endothelial cells. Researchers were successful in generating a functional vascular tree, but only in a complex, ill-defined experimental gel scaffold. It was necessary to add a number of differentiation-promoting factors, some of which are not well defined, in order to induce the isolated single cells into a vessel structure (Lawley T J and Kubato Y J. Invest Derm. 93:59S–61S 1989, Schechner J S et al. PNAS 97:9191–9196, 2000). In one study, it was necessary to transfect a gene that blocked apoptosis (or programmed cell death) into cultured endothelial cells in order for the vasculature to persist in the implant (Nor J E et al., Lab Invest. 81:453–463 2001; Schechner J S et al. PNAS 97:9191–9196, 2000).

Additionally, in tissues and organs suffering from the consequences of chronic ischemic disease such as after myocardial infarction or peripheral vascular disease, expansion of the vasculature adjacent to the effected tissue areas into the ischemic zones offers one mechanism by which these tissues can be recovered. Thus, there exists a need for methods and compositions for vascularizing tissue engineered constructs and donated tissues and organs and for revascularizing diseased or dysfunctional tissues and organs. Preferably, such methods and materials would not require the incorporation of genetically engineered cells to avoid premature apoptosis.

SUMMARY OF THE INVENTION

This application discloses methods and materials by which functional microvascular beds can be preformed in the laboratory for use in engineered tissue constructs and therapeutic applications. According to certain embodiments of the invention, a fully developed vascular network forms and persists in a simple, host-derived matrix and without the need to genetically engineer the vessels. The core technology of the process involves the expansion of a collection of isolated capillary fragments into an intact, functional capillary bed. Capillary fragments are purified and collected from a vascular tissue, usually adipose tissue, and placed into a three dimensional culture environment that, in certain embodiments, comprises a collagen I gel (Hoying et al., In Vitro 32:409–419, 1996). These fragments sprout and grow by day 4 in this culture environment, ultimately establishing a new microvascular (capillary) bed by day 11 (see FIG. 1). This new vasculature has all of the structural and cellular features of a viable capillary bed observed in the body (Id.). Cultured vessels are on average 15 microns in outer diameter, contain patent lumen, have endothelial cells oriented along the long axis of the vessels and extra-capillary mural cells covering the endothelial cell-formed tubes.

In certain embodiments, the present invention provides engineered microvascular networks, also referred to as "prevascularized constructs", that will connect with the vasculature of a host animal following implantation and carry blood (see FIG. 2). Furthermore, the capillaries present in the construct prior to implantation subsequently result in the formation of a mature and functional vascular network (arteries, arterioles, capillaries and veins) required for proper tissue perfusion and health (see FIG. 3). This is supported by data obtained in experimental animal models.

The new capillary beds can be generated from rat-derived vessel fragments. However human-derived vessel fragments may also be used in the same process. Additionally, the inventors envision a process by which microvessel fragments are isolated from a patient's adipose tissue harvested by liposuction. To isolated microvessel fragments, the method of isolating single endothelial cells may be used as described in U.S. Pat. No. 5,957,972, the entire contents of which are incorporated by reference. Harvested vessel fragments would be placed into a three-dimensional culture using fibrin derived from the patient's own blood as the 3-D matrix scaffold. In this manner, a patient would receive his own (autologous) vessels after a brief culture period (e.g., one hour to 30 days).

The methods and compositions disclosed herein may be used in tissue engineering, as an implant for stimulating angiogenesis in neighboring host tissues, and as a means for delivering recombinant gene products throughout the body. In certain embodiments, these methods and compositions include mixing in stromal cells with the vascular elements and determining cell viability and function. Initial cell types to be examined are muscle precursor stem cells and pancreas β-islet cells, to name a few. Furthermore, the nature of the resulting vasculature present in the construct following implantation into a host animal can be characterized. Additionally, a variety of scaffold matrices including fibrin gels and artificial, FDA-approved synthetic biocompatible polymers may be used.

I. Prevascularization of Engineered Tissues and Organs.

In certain embodiments, the above-described process could be incorporated into tissue building methods to establish, prior to implantation, a functional vasculature within a tissue engineered organ or tissue. Characterization of the capillary bed formed in culture and the resulting vasculature present after implantation indicates that the cultured vessels have the potential to differentiate or change into the type of vasculature required to meet specific tissue needs. What this implies is that it may be possible to affect changes to this basic "foundation" microvasculature built in the lab and impart a new character to the microvascular bed to match the type of tissue being built. For example, engineered heart muscle will have a relatively high capillary density while the vasculature of a liver organoid will exhibit a typical sinusoid-like character. The pre-vascularization process disclosed herein has great potential to incorporate a vascular network within an engineered tissue and engineer it to match a particular tissue of interest, thus overcoming a significant hurdle in tissue engineering.

Thus, methods for stimulating or inducing the vascularization of engineered tissues are provided. In certain embodiments, the prevascularized construct is incorporated into the tissue engineering process to create a functional vasculature within the engineered tissue. In other embodiments, at least one prevascular construct is placed on at least one surface of, or adjacent to, at least one engineered tissue. In certain embodiments, the engineered tissue(s) is vascularized post-implantation.

II. Stimulus for Tissue Revascularization.

In tissues suffering from the consequences of chronic ischemic disease, such as after myocardial infarction or peripheral vascular disease, expansion of the vasculature adjacent to the effected tissue areas into the ischemic zones offers one mechanism by which these tissues can be recovered. Implantation of the prevascularized construct could act as a stimulus and nidus for revascularization of the affected areas. In this regard, the implant would act as a nucleus of vascular growth, rapidly establishing a new vascular network within the previously avascular or "hypo-vascular" zone. We have evidence that the presence of the engineered vessels preserves the surrounding tissue integrity (see FIG. 3). We believe that insertion of these prevascularized constructs will not only provide for a rapid reperfusion of injured tissues, but may also support the restructuring and repair of those tissues. By incorporating stem cells, progenitor cells or Relevant Cells into the prevascularized construct, cells useful for restructuring, repairing and/or repopulating damaged tissues or organs are provided. In certain embodiments, methods for stimulating or inducing the revascularization of at least one tissue or at least one organ are provided. In certain embodiments, the tissue or organ may be ischemic and/or have a zone or region that is avascular or hypovascular, for example, but not limited to, chronic ischemic disease such as after myocardial infarction, peripheral vascular disease, or cerbrovascular accident (stroke).

III. Gene Product Delivery.

Current gene therapy strategies suffer from difficulties in successfully getting the desired gene incorporated into cells of the patient and the therapeutic protein (produced by the recombinant gene) distributed throughout the body. Use of these prevascularized constructs in gene delivery provides 1) a means by which genetically engineered cells included in the tissue construct have ready access to a blood stream (molecular exchange to and from the blood stream occurs best in capillaries) and 2) the culture vessel elements themselves are amenable to genetic engineering and may act as the source of therapeutic gene product. Prevascularized constructs provide a potential means to solving this problem.

In certain embodiments, prevascularized constructs comprising genetically engineered cells are disclosed. Such prevascularized constructs comprising genetically engineered cells are useful in the vascularization and revascularization methods of the invention.

DESCRIPTION OF EXEMPLARY EMBODIMENTS

Figure 1:
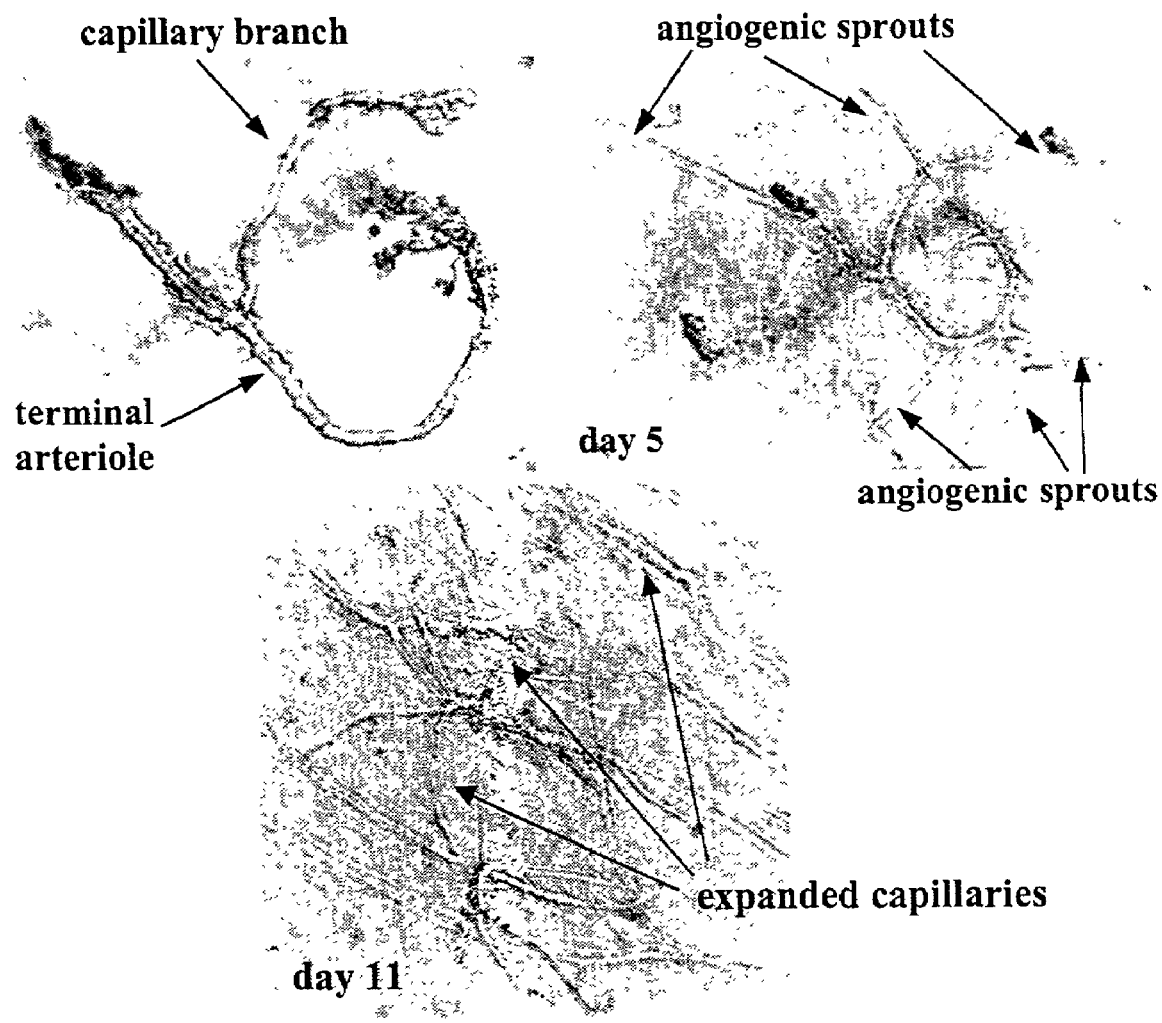
FIG. 1 depicts the expansion of microvessel fragments into a functional capillary bed. Vessel fragments undergo sprouting (day 4), as shown in the upper right panel, and eventually grow into an elaborate capillary tree (day 11), as shown in the lower panel.
Figure 2:
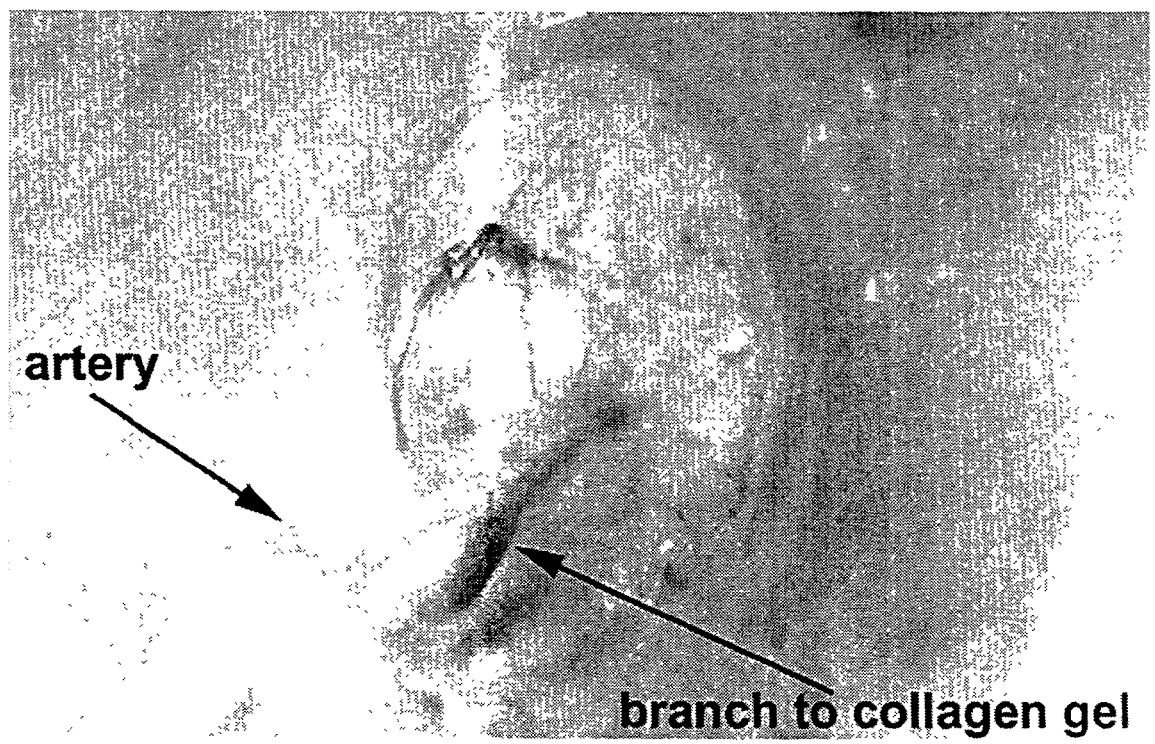
FIG. 2 depicts a prevascularized construct 14 days after implantation. The engineered tissue is flushed, indicating the presence of blood within the simple tissue. Furthermore, a feed vessel has grown into the construct.
Figure 3:
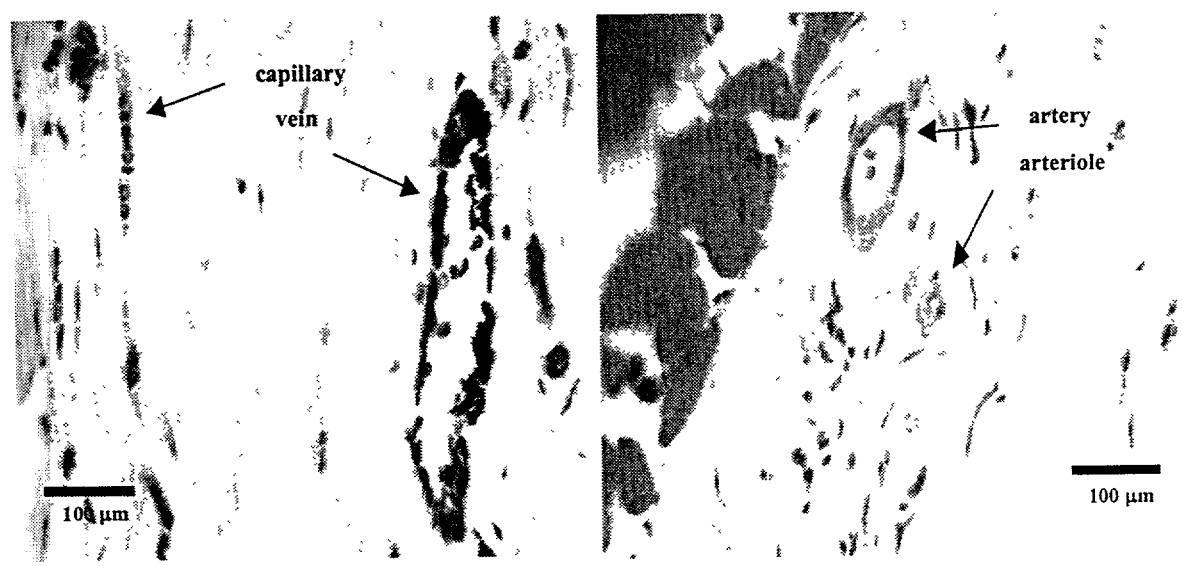
FIG. 3 shows the development of mature vessel elements into a functional vasculature within the implant. The vasculature consists of input vessels (artery), as indicated by the "artery" arrow in the right-hand panel, exchange vessels (capillary), and draining vessels (vein), as indicated by the "capillary" and "vein" arrows in the left-hand panel.

The section headings used herein are for organizational purposes only and are not to be construed as limiting the subject matter described. All references cited in this application are expressly incorporated by reference for any purpose.

The term "three-dimensional culture" is used in the broad sense herein and refers to a composition comprising a biocompatible matrix, scaffold, or the like. The three-dimensional culture may be liquid, gel, semi-solid, or solid at 25° C. The three-dimensional culture may be biodegradable or non-biodegradable. Exemplary three-dimensional culture materials include polymers and hydrogels comprising collagen, fibrin, chitosan, MATRIGEL, polyethylene glycol, dextrans including chemically crosslinkable or photocrosslinkable dextrans, and the like. In certain embodiments, the three-dimensional culture comprises allogeneic components, autologous components, or both allogeneic components and autologous components. In certain embodiments, the three-dimensional culture comprises synthetic or semi-synthetic materials. In certain embodiments, the three-dimensional culture comprises a framework or support, such as a fibrin-derived scaffold. The term "scaffold" is also used in a broad sense herein. Thus scaffolds include a wide variety of three-dimensional frameworks, for example, but not limited to a mesh, grid, sponge, foam, or the like.

The terms "engineered tissue", "engineered tissue construct", or "tissue engineered construct" as used herein refer to a tissue or organ that is produced, in whole or in part, using tissue engineering techniques. Descriptions of these techniques can be found in, among other places, "Principles of Tissue Engineering, 2d ed.", Lanza, Langer, and Vacanti, eds., Academic Press, 2000 (hereinafter "Lanza et al."); "Methods of Tissue Engineering", Atala and Lanza, eds., Academic Press, 2001 (hereinafter "Atala et al."); Animal Cell Culture, Masters, ed., Oxford University Press, 2000, (hereinafter "Masters"), particularly Chapter 6; and U.S. Pat. No. 4,963,489 and related U.S. patents.

The term "microvessel fragment" as used herein refers to a segment or piece of vascular tissue, including at least a part or segment of at least one artery, arteriole, capillary, venule, or vein. Typically a microvessel includes endothelial cells arranged in a tube surrounded by one or more layers of mural cells, such as smooth muscle cells or pericytes, and may further comprise extracellular matrix components, such as basement membrane proteins. In certain embodiments, the microvessel fragments are obtained from vascular tissue, for example, but not limited to, skin, skeletal muscle, cardiac muscle, the atrial appendage of the heart, lung, mesentery, or adipose tissue. In certain embodiments, the adipose tissue microvessel fragments are obtained from, for example, but not limited to, subcutaneous fat, perirenal fat, pericardial fat, omental fat, breast fat, epididymal fat, properitoneal fat, and the like. The skilled artisan will appreciate that other fat deposits or any vascular-rich tissue or organ may serve as a source of microvessel fragments for use in the invention, for example, but not limited to, skin, muscle, including skeletal or cardiac muscle, lung, and mesentery. In certain embodiments, the microvessel fragments are obtained from adipose tissue harvested by liposuction or abdominoplasty. Adipiose tissue harvested by a liposuction procedure where a sonic probe is not used during the harvesting process is particularly useful.

The terms "vascularize", "vascularizing", or "vascularization" as used herein refer to providing a functional or substantially functional vascular network to an organ or tissue, particularly an engineered tissue. A functional or substantially functional vascular network is one that perfuses or is capable of perfusing the tissue or organ to meet some or all of the tissue's or organ's nutritional needs, oxygen demand, and waste product elimination needs. A vascular tissue is a natural tissue that is rich in vascular elements, such as microvessels, for example, but without limitation, adipose tissue.

The terms "revascularize", "revascularizing", "neovascularization", or "revascularization" as used herein refer to revising an existing vascular network or establishing a new functional or substantially functional vascular network in a tissue or organ that has an avascular or hypovascular zone, typically due to disease, congenital defect, or injury. Additionally, the topical application of certain chemotherapeutic agents, for example, but not limited to, 5-flourouracil (5-FU), may also result in an ischemic or avascular zone. Such an avascular or hypovascular tissue or organ is often totally or partially dysfunctional or has limited function and may be in need of revascularization. Revascularizing such a tissue or organ may result in restored or augmented function.

As used herein, the term "polymer" is used in the broad sense and is intended to include a wide range of biocompatible polymers, for example, but not limited to, homopolymers, co-polymers, block polymers, cross-linkable or crosslinked polymers, photoinitiated polymers, chemically initiated polymers, biodegradable polymers, nonbiodegradable polymers, and the like. In other embodiments, the prevascularized construct comprises a polymer matrix that is nonpolymerized, to allow it to be combined with a tissue, organ, or engineered tissue in a liquid or semi-liquid state, for example, by injection. In certain embodiments, the prevascularized construct comprising liquid matrix may polymerize or substantially polymerize "in situ." In certain embodiments, the prevascularized construct is polymerized or substantially polymerized prior to injection. Such injectable compositions are prepared using conventional materials and methods know in the art, including, but not limited to, Knapp et al., Plastic and Reconstr. Surg. 60:389–405, 1977; Fagien, Plastic and Reconstr. Surg. 105: 362–73 and 2526–28, 2000; Klein et al., J. Dermatol. Surg. Oncol. 10:519–22,1984; Klein, J. Amer. Acad. Dermatol. 9:224–28, 1983; Watson et al., Cutis 31:543–46,1983; Klein, Dermatol. Clin. 19:491–508, 2001; Klein, Pedriat. Dent. 21:449–50, 1999; Skorman, J. Foot Surg. 26:511–5, 1987; Burgess, Facial Plast. Surg. 8:176–82, 1992; Laude et al., J. Biomech. Eng. 122:231–35, 2000; Frey et al., J. Urol. 154:812–15, 1995; Rosenblatt et al., Biomaterials 15:985–95, 1994; Griffey et al., J. Biomed. Mater. Res. 58:10–15, 2001; Stenburg et al., Scfand. J. Urol. Nephrol. 33:355–61, 1999; Sclafani et al., Facial Plast. Surg. 16:29–34, 2000; Spira et al., Clin. Plast. Surg. 20:181–88,1993; Ellis et al., Facila Plast. Surg. Clin. North Amer. 9:405–11, 2001; Alster et al., Plastic Reconstr. Surg. 105:2515–28, 2000; and U.S. Pat. Nos. 3,949,073 and 5,709,854.

In certain embodiments, the polymerized or nonpolymerized matrix comprises collagen, including contracted and non-contracted collagen gels, hydrogels comprising, for example, but not limited to, fibrin, alginate, agarose, gelatin, hyaluronate, polyethylene glycol (PEG), dextrans, including dextrans that are suitable for chemical crosslinking, photo-crosslinking, or both, albumin, polyacrylamide, polyglycolyic acid, polyvinyl chloride, polyvinyl alcohol, poly(n-vinyl-2-pyrollidone), poly(2-hydroxy ethyl methacrylate), hydrophilic polyurethanes, acrylic derivatives, pluronics, such as polypropylene oxide and polyethylene oxide copolymer, or the like. In certain embodiments, the fibrin or collagen is autologous or allogeneic with respect to the intended recipient. The skilled artisan will appreciate that the matrix may comprise non-degradable materials, for example, but not limited to, expanded polytetrafluoroethylene (ePTFE), polytetrafluoroethylene (PTFE), polyethyleneterephthalate (PET), polyurethane, polyethylene, polycabonate, polystyrene, silicone, and the like, or selectively degradable materials, such as poly (lactic-co-glycolic acid; PLGA), PLA, or PGA. (See also, Middleton et al., Biomaterials 21:2335–2346, 2000; Middleton et al., Medical Plastics and Biomaterials, March/April 1998, at pages 30–37; Handbook of Biodegradable Polymers, Domb, Kost, and Domb, eds., 1997, Harwood Academic Publishers, Australia; Rogalla, Minim. Invasive Surg. Nurs. 11:67–69, 1997; Klein, Facial Plast. Surg. Clin. North Amer. 9:205–18, 2001; Klein et al., J. Dermatol. Surg. Oncol. 11:337–39, 1985; Frey et al., J. Urol. 154:812–15, 1995; Peters et al., J. Biomed. Mater. Res. 43:422–27, 1998; and Kuijpers et al., J. Biomed. Mater. Res. 51:136–45, 2000).

I. Prevascularized Constructs.

The terms "prevascularized construct" or "engineered microvascular network" refers to a composition comprising at least one microvessel fragment, typically isolated from a vascular-rich tissue, in a three-dimensional culture, including but not limited to a matrix, scaffold, gel, or liquid. In certain embodiments, the prevascularized constructs comprise a three-dimensional matrix and microvessel fragments. In certain embodiments, the matrix comprises a preformed framework, for example, but not limited to a fibrin scaffold. In certain embodiments, the three-dimensional culture comprises a polymerized, substantially polymerized, or nonpolymerized matrix.

In certain embodiments, prevascularized constructs are prepared by combining microvessel fragments and a liquid three-dimensional culture, such as nonpolymerized collagen, agarose, gelatin, other nonpolymerized polymer matrices, or the like. In other embodiments, the microvessel fragments are seeded, sodded or perfused onto or through a solid or semi-solid three-dimensional culture environment, for example, but not limited to, a framework, scaffold, hollow-fiber filter, or the like.

Prevascularized constructs may be categorized as "cultured microvessel constructs" or "freshly isolated microvessel constructs." A cultured microvessel construct is typically incubated prior to implantation. For example, but not limited to, in a humidified incubator at 37° C. and 5% $CO_2$. Typically such cultured microvessel constructs are incubated for a period of one hour to thirty days, but may be incubated for shorter or longer periods, as desired. The skilled artisan will appreciate that the term "cultured" may or may not refer to the use of conventional incubation methods, such as a controlled-temperature incubator. Alternately, a prevascularized construct may comprise a freshly isolated microvessel construct that undergoes little or no incubation prior to use. The skilled artisan will appreciate that freshly isolated microvessel constructs may, but need not, be incubated. In certain embodiments, a freshly isolated microvessel construct comprises microvessel fragments in a three-dimensional culture that has been "incubated" subsequent to the introduction of the microvessels, for example, but without limitation, to allow the construct to polymerize. In other embodiments, a freshly isolated microvessel construct comprises a liquid three-dimensional culture, as may be appropriate for implantation by injection (see, e.g., U.S. Pat. Nos. 5,709,854 and 6,224,893). Such liquid constructs may, but need not, polymerize in situ under appropriate conditions.

The skilled artisan will understand that prevascularized constructs comprising a nonpolymerized liquid three-dimensional culture that is subsequently allowed to polymerize or gel are capable of assuming a multitude of shapes. Thus, in certain embodiments, the ultimate size and shape of the polymerized construct depends, in part, on the size and shape of the vessel in which the construct is polymerized. For example, but not limited to, cylindrical or tubular constructs can be prepared using conical tubes; disk-shaped constructs can be prepared using multi-well plates; planar constructs can be prepared using flat surfaces, for example, a petri dish, the inverted lid of a multi-well plate, or a flat-bottomed dish. Additionally, in certain embodiments, polymerized prevascularized constructs can be cut or trimmed into a desired size or shape. Thus, prevascularized constructs can be prepared in virtually any size and shape, prior to or during use.

In certain embodiments, the prevascularized construct comprises autologous microvessel fragments in an autologous or substantially autologous three-dimensional culture. In certain embodiments, prevascularized constructs comprise microvessel fragments in a three-dimensional culture comprising a scaffold, for example, but not limited to, fibrin-derived scaffolds (see, e.g., Nicosia et al., Lab. Invest. 63:115–22, 1990) and scaffolds comprising artificial, FDA-approved synthetic biocompatible polymers, for example, but not limited to, polyethylene, polymethacrylate, polyurethane, vinyl, such as polyvinyl chloride, silicones, PLGA, PTFE, ePTFE, polypropylene, polyethyleneterephthalate (PET), nylon, polylactide, and polyglycolide. Discussions of exemplary biocompatible polymers, scaffolds, and other matrix materials, including protocols for their preparation and use, may be found in, among other places, Atala et al., particularly Chapters 42–76; Lanza et al., particularly Chapters 21 and 22; and Handbook of Biodegradable Polymers, Domb, Kost, and Domb, eds., 1997, Harwood Academic Publishers, Australia.

In certain embodiments, the prevascularized constructs comprise microvessel fragments that are autologous or allogeneic with respect to the intended human or animal recipient. In certain embodiments, the prevascularized construct further comprises at least one cytokine, at least one chemokine, at least one antibiotic, such as an antimicrobial agent, at least one drug, at least one analgesic agent, at least one anti-inflammatory agent, at least one immunosuppressive agent, or various combinations thereof. In certain embodiments, the at least one cytokine, at least one antibiotic, at least one drug, at least one analgesic agent, at least one anti-inflammatory agent, at least one immunosuppressive agent, or various combinations thereof comprise a controlled-release format, such as those generally known in the art, for example, but not limited to, Richardson et al., Nat. Biotechnol. 19:1029–34, 2001.

Exemplary cytokines include angiogenin, vascular endothelial growth factor (VEGF, including, but not limited to VEGF-165), interleukins, fibroblast growth factors, for example, but not limited to, FGF-1 and FGF-2, hepatocyte growth factor, (HGF), transforming growth factor beta (TGF-β), endothelins (such as ET-1, ET-2, and ET-3), insulin-like growth factor (IGF-1), angiopoietins (such as Ang-1, Ang-2, Ang3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PDECGF), placenta growth factor (PLGF), and the like. Cytokines, including recombinant cytokines, and chemokines are typically commercially available from numerous sources, for example, R & D Systems (Minneapolis, Minn.); Endogen (Woburn, Wash.); and Sigma (St. Louis, Mo.). The skilled artisan will understand that the choice of chemokines and cytokines for incorporation into particular prevascularized constructs will depend, in part, on the target tissue or organ to be vascularized or revascularized.

In certain embodiments, prevascularized constructs further comprise at least one genetically engineered cell. In certain embodiments, prevascularized constructs comprising at least one genetically engineered cell will constitutively express or inducibly express at least one gene product encoded by the at least one genetically engineered cell due to the genetic alterations within the at least one genetically engineered cell induced by techniques known in the art. Descriptions of exemplary genetic engineering techniques can be found in, among other places, Ausubel et al., Current Protocols in Molecular Biology (including supplements through March 2002), John Wiley & Sons, New York, N.Y., 1989; Sambrook et al., Molecular Cloning: A Laboratory Manual, $2^{nd}$ Ed., Cold Spring Harbor Laboratory Press, Cold Spring Harbor, N.Y., 1989; Sambrook and Russell, Molecular Cloning: A Laboratory Manual, $3^{rd}$ Ed., Cold Spring Harbor Laboratory Press, Cold Spring Harbor, N.Y., 2001; Beaucage et al., Current Protocols in Nucleic Acid Chemistry, John Wiley & Sons, New York, N.Y., 2000 (including supplements through March 2002); Short Protocols in Molecular Biology, $4^{th}$ Ed., Ausbel, Brent, and Moore, eds., John Wiley & Sons, New York, N.Y., 1999; Davis et al., Basic Methods in Molecular Biology, McGraw Hill Professional Publishing, 1995; Molecular Biology Protocols (see the highveld.com website), and Protocol Online (protocol-online.net). Exemplary gene products for genetically modifying the genetically engineered cells of the invention include, plasminogen activator, soluble CD-4, Factor VIII, Factor IX, von Willebrand Factor, urokinase, hirudin, interferons, including alpha-, beta- and gamma-interferon, tumor necrosis factor, interleukins, hematopoietic growth factor, antibodies, glucocerebrosidase, adenosine deaminase, phenylalanine hydroxylase, human growth hormone, insulin, erythropoietin, VEGF, angiopoietin, hepatocyte growth factor, PLGF, and the like.

In certain embodiments, the prevascularized construct further comprises appropriate stromal cells, stem cells, Relevant Cells, or combinations thereof. As used herein, the term "stem cells" is used in a broad sense and includes traditional stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu. Rev. Cell. Dev. Biol. 17:387–403; Pittinger et al., Science, 284:143–47, 1999; Animal Cell Culture, Masters, ed., Oxford University Press, 2000; Jackson et al., PNAS 96(25):14482–86, 1999; Zuk et al., Tissue Engineering, 7:211–228, 2001 ("Zuk et al."); Atala et al., particularly Chapters 33–41; and U.S. Pat. Nos. 5,559,022, 5,672,346 and 5,827,735. Descriptions of stromal cells, including methods for isolating them, may be found in, among other places, Prockop, Science, 276:71–74, 1997; Theise et al., Hepatology, 31:235–40, 2000; Current Protocols in Cell Biology, Bonifacino et al., eds., John Wiley & Sons, 2000 (including updates through March, 2002); and U.S. Pat. No. 4,963,489. The skilled artisan will understand that the stem cells and/or stromal cells selected for inclusion in a prevascularized construct are typically appropriate for the intended use of that construct.

The term "Relevant Cells", as used herein refers to cells that are appropriate for incorporation into a prevascularized construct, based on the intended use of that construct. For example, Relevant Cells that are appropriate for the repair, restructuring, or repopulation of damaged liver may include, without limitation, hepatocytes, biliary epithelial cells, Kupffer cells, fibroblasts, and the like. Exemplary Relevant Cells for incorporation into prevascularized constructs include neurons, myocardiocytes, myocytes, chondrocytes, pancreatic acinar cells, islets of Langerhans, osteocytes, hepatocytes, Kupffer cells, fibroblasts, myocytes, myoblasts, satellite cells, endothelial cells, adipocytes, preadipocytes, biliary epithelial cells, and the like. These types of cells may be isolated and cultured by conventional techniques known in the art. Exemplary techniques can be found in, among other places, Atala et al., particularly Chapters 9–32; Freshney, Culture of Animal Cells A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

The skilled artisan will appreciate that such stromal cells, stem cells, and/or Relevant Cells may be incorporated into the prevascularized constructs during or after preparation. For example, but not limited to, combining microvessel fragments, stem cells, Relevant Cells, and/or stromal cells in a liquid three-dimensional culture, such as collagen, fibrin, or the like, or seeding or sodding stem cells, Relevant Cells, and/or stromal cells in or on a prevascularized construct may be achieved. Exemplary combinations of appropriate stem cells, stromal cells, and Relevant Cells for incorporation into prevascularized constructs include: islets of Langerhans and/or pancreatic acinar cells in a prevascularized construct for revascularizing a damaged pancreas; hepatocytes, hepatic progenitor cells, Kupffer cells, endothelial cells, endodermal stem cells, liver fibroblasts, and/or liver reserve cells in a prevascularized construct for revascularizing a damaged liver For example, but not limited to, appropriate stem cells or stromal cells for a prevascularized construct for vascularizing, repairing, and reconstructing a damaged or disease liver might comprise liver reserve cells, liver progenitor cells, such as, but not limited to, liver fibroblasts, embryonic stem cells, liver stem cells; cardiomyocytes, Purkinje cells, pacemaker cells, myoblasts, mesenchymal stem cells, satellite cells, and/or bone marrow stem cells for revascularizing a damaged or ischemic heart (see, e.g., Atkins et al., J. of Heart and Lung Transplantation, December 1999, at pages 1173–80; Tomita et al., Cardiovascular Research Institute, American Heart Association, 1999, at pages 92–101; Sakai et al., Cardiovascular Research Institute, American Heart Association, 1999, at pages 108–14); and the like.

II. Methods for Vascularizing Engineered Tissues and Organs

In certain embodiments, methods are provided for vascularizing engineered tissues comprising combining at least one prevascularized construct with an engineered tissue to produce a vascularized engineered tissue. In certain embodiments, prevascularized constructs for vascularizing engineered tissues further comprise at least one stromal, stem cell, Relevant Cell, or genetically engineered cell. In certain embodiments, prevascularized construct for vascularizing engineered tissues comprise at least one cytokine, chemokine, antibiotic, drug, analgesic, antiinflammatory, or the like. Methods for preparing engineered tissues are well known in the art. Descriptions of such techniques may be found in, among other places, Atala et al.; Lanza et al.; Masters; and in U.S. Pat. Nos. 4,963,489; 5,266,480; 5,510,254; 5,512,475; 5,516,680; 5,516,681; 5,518,915; 5,541,107; 5,578,485; 5,624,840; 5,763,267;5,785,964; 5,792,603; 5,842,477; 5,858,721; 5,863,531; 5,902,741; 5,962,325; 6,022,743; 6,060,306; 6,121,042; and 6,218,182.

According to certain methods for vascularizing engineered tissues, the term "combining" comprises placing or implanting at least one prevascularized construct on any surface of, within, between layers of, or adjacent to, said engineered tissue. In certain embodiments, combining comprises coating the engineered tissue with a prevascularized construct. For example, but without limitation, an engineered tissue is dipped into a liquid prevascularized construct or a liquid prevascularized construct is poured or sprayed on an engineered tissue. In certain embodiments, such liquid prevascularized construct coating the engineered tissue is polymerized. In certain embodiments, such coated engineered tissues are incubated prior to implantation into a recipient animal or human. In certain embodiments, the prevascularized construct is combined with the engineered tissue by injection. In certain embodiments, such injected construct polymerizes in situ, following injection. In certain embodiments, such injected prevascularized construct comprises at least one cultured microvessel construct, at least one freshly isolated microvessel construct, or both.

In certain embodiments, combining at least one prevascularized with an engineered tissue comprises attaching at least one prevascularized construct to at least one engineered tissue, using techniques known in the art. Exemplary attachment means include suturing, stapling, for example, with surgical staples, glue or adhesive, such as surgical glue, biochemical interactions such as with the extracellular matrix, photo-activated glue, fibrin glue, acrylate-based adhesives, and the like.

In certain embodiments, combining comprises placing the at least one prevascularized construct between the layers of an engineered tissue, such that at least one surface of at least one prevascularized construct is adjacent to, or in contact with, at least one surface of at least one engineered tissue. In certain embodiments, combining comprises inserting or implanting at least one prevascularized construct within an engineered tissue, for example, but not limited to, within a designed pocket, bore, crevice, or the like. In certain embodiments, the prevascularized construct is inserted within an incision in the engineered tissue. In certain embodiments, combining comprises wrapping at least one prevascularized construct around or within at least one engineered tissue, such that the prevascularized construct envelopes or substantially envelopes the engineered tissue, or is enveloped or substantially enveloped by the engineered tissue. In certain embodiments, combining comprises forming or incorporating at least one prevascularized construct into the engineered tissue during the tissue engineering process. In certain embodiments, combining comprises culturing at least one prevascularized construct on or within a growing engineered tissue during the tissue engineering process, such as in a bioreactor. In certain embodiments, at least one prevascularized construct is enveloped or substantially enveloped by the adjacent tissue or organ during the tissue engineering process.

In certain embodiments, the combined engineered tissue and at least one prevascularized construct are incubated, for example within a bioreactor or humidified incubator, prior to in vivo implantation into a recipient animal or human. In certain embodiments, combining comprises implanting at least one engineered tissue comprising at least one prevascularized construct directly into a recipient animal or human with little or no additional incubation.

In certain embodiments, the implanted prevascularized construct serves as a nucleation site for vascularizing the engineered tissue. In certain embodiments, appropriate stromal cells, stem cells, and/or Relevant Cells from the prevascularized construct will support the integration of the engineered tissue within the recipient animal or human. Constructs comprising genetically engineered cells may produce recombinant products that are distributed systemically via the bloodstream or delivered to the local microenvironment to induce repair, wound healing, or the like.

III. Methods for Revascularizing Damaged or Injured Tissues or Organs

In certain embodiments, methods for revascularizing damaged or injured tissues or organs, i.e., tissues or organs in need of revascularization and repair or reconstruction, are provided. In certain embodiments, prevascularized constructs for revascularizing tissues or organs further comprise at least one appropriate stromal cell, stem cell, Relevant Cell, or genetically engineered cell. In certain embodiments, prevascularized constructs for revascularizing tissues or organs comprise at least one cytokine, chemokine, antibiotic, drug, analgesic, anti-inflammatory, or the like. In certain embodiments, the prevascularized construct, once implanted in vivo, will develop a functional vascular bed and inosculate with the surrounding functional vascular system and perfuse, or be capable of perfusing, the damaged tissue or organ.

According to certain methods for revascularizing tissues or organs, at least one prevascularized construct is combined with said tissue or organ and a revascularized tissue or organ is generated. According to certain methods for revascularizing tissues or organs, the term "combining" comprises placing or implanting at least one prevascularized construct on any surface of, within, between the layers of, or adjacent to, said tissue or organ. In certain embodiment, the prevascularized construct is implanted in the tissue or organ by injection. In certain embodiments, such injected construct will polymerize in situ, following implantation. In certain embodiments, such injected prevascularized construct comprises at least one cultured microvessel construct, at least one freshly isolated microvessel construct, or both. In certain embodiments, combining comprises attaching at least one prevascularized construct to at least one tissue or organ in need of revascularizing, using techniques known in the art, such as described above.

The skilled artisan understands that certain tissues and organs are covered by or contain a layer of fibrous tissue, connective tissue, fatty tissue, or the like, and that the underlying tissue or organ can be revascularized without removing this layer. Such a layer may be naturally occurring (such as a serosal layer, mucous membrane, fibrous capsule, or the like), may result form fibrosis, necrosis, or ischemia, due to disease, defect, injury, or biochemical deficiency. Typically, the microvessel fragments of the prevascularized construct can penetrate such a layer and inosculate with the vasculature of the underlying tissue or organ, revascularizing the tissue or organ. Thus, combining the prevascularized construct with the tissue or organ in need of revascularization, comprises placing the prevascularized construct on or in such layer. For example, but not limited to, placing the prevascularized construct on: the meninges to revascularize brain tissue; the epicardium to revascularize the myocardium; the peritoneum and/or serosa, to revascularize portions of the large intestine; the conjunctiva and/or subconjunctiva to revascularize the eye; the tracheal surface to revascularize the trachea; the bucchal mucosa to revascularize the mouth; the pleural and/or serosal surface to revascularize the lung; the pleural and/or peritoneal surface to revascularize the diaphragm; the skin to revascularize nonhealing skin ulcers, such as diabetic ulcers; the pericardial surface to revascularize the pericardium; and the like.

In certain embodiments, the prevascularized construct, when combined with the tissue or organ within the animal or human, will develop functional vascular bed and inosculate with the surrounding functional vascular system and perfuse the damaged tissue or organ. In certain embodiments, the implanted prevascularized construct serves as a nucleation site for revascularizing the damaged tissue or organ. In certain embodiments, appropriate stem cells, stromal cells, and/or Relevant Cells from the prevascularized construct will support the restructuring and repair of the damaged tissue or organ. Constructs comprising genetically engineered cells may produce recombinant products that are distributed systemically via the bloodstream or delivered to the local microenvironment to induce repair, wound healing, or the like.

The invention, having been described above, may be better understood by reference to examples. The following examples are intended for illustration purposes only, and should not be construed as limiting the scope of the invention in any way.

EXAMPLES

Example 1

We have developed a microvascular construct consisting of cultured microvessel in a 3-dimensional collagen matrix. The construct is prepared from ratderived, freshly isolated, intact microvessel fragments (arterioles, capillaries and venules), which are subsequently cultured in a collagen I matrix. After 7–10 days, these fragments expand into an extensive, patent 3-dimensional capillary like network containing both endothelial cells and mural cells. Subcutaneous transplantation of mature microvascular constructs into SCID mice for 14 days resulted in the perfusion of blood within vessels of the construct as detected by laser-Doppler perfusion imaging (LDPI), and Orthoganol Polarization Spectroscopy (OPS). The presence of RBCs within vessels was confirmed by hemotoxylin and eosin (H&E) staining. Control collagen gels lacking microvessel remained avascular and partially degraded. Evaluation of transplanted constructs over time revealed blood flow within vessels as early as 3 days post-transplantation. These results suggest that prevascularized tissue constructs may accelerate the establishment of blood perfusion through the construct following transplantation.

Example 2

Rat Microvessel Isolation and Preparation of Cultured Microvessel Constructs

Rat fat microvessel fragments (RFMF) were isolated from the epididymal fat pads (8 to 10 milliliters (mLs)) of retired breeder Sprague Dawley or Fischer 344 rats, essentially as described (Carter et al., Surgery, 120:1089–94, 1996). Harvested fat pads were washed in EFAF-PBS (Dulbecco's cation-free phosphate buffered saline (DCF-PBS) supplemented with 0.1% essentially fatty acid free BSA (EFAFBSA; fraction V Sigma, St. Louis, Mo.), finely minced, placed in an Erlenmeyer flask containing a stir bar, and digested in PBS supplemented with 2 mg/mL collagenase (Worthington Biochemicals) and 2 mg/mL bovine serum albumin (BSA) for 10 minutes at 37° C. with shaking for mechanical-assisted enzymatic disruption. The solution was placed in a room temperature centrifuge and the microvessel fragments were pelleted at 700× g for 3 minutes. Vessel fragments were transferred to 15 or 50 mL polypropylene conical tubes (Falcon), washed using approximately 12 mLs of EFAF-PBS and separated from adipose cells by centrifugation in an IEC tabletop centrifuge at 600–700× g for 3 minutes. Following centrifugation the fat cake was removed by decanting and the pelleted microvessel fragments were suspended in 12 ml EFAF-PBS. Tissue debris and large vessel pieces were removed by filtering through a nylon screen of 500 μm pore size. RFMF were collected from the filtrate by screening the filtrate through a nylon screen of 30 micron pore size. The RFMF were collected from the screen, placed in 15 mL polypropylene conical tubes, washed twice by pipetting using approximately 12 mLs of EFAF-PBS per wash, and centrifuged as before.

A nonpolymerized collagen solution was prepared by mixing the appropriate volume of stock rat tail collagen I stock (4 mg/ml) in 0.2N HCl (BD Biosciences, Bedford, Mass.) with 4× concentration of DMEM culture medium (Gibco BRL) to produce a final concentration of 3 mg/ml collagen in DMEM. This solution was placed on ice and the pH was neutralized by adding approximately 12 μL of 1 M NaOH per ml of collagen solution. The pH indicator in the DMEM changed from yellow (acidic) to red (neutral). Final collagen concentrations of greater than 1.5 mg/mL and less than 4 mg/mL produce robust microvessel fragment growth and angiogenesis.

The washed RFMF were counted using phase contrast microscopy and resuspended in the liquid collagen solution at a concentration of approximately 12,000–15,000 RFMF/mL. This liquid prevascularized construct was plated into wells of 48 well tissue culture plates and placed in a humidified, 37° C. incubator for 15–30 minutes to polymerize the construct. When the prevascularized construct was polymerized, an equal volume (approximately 0.2 mL) Dulbecco's modified Eagle's medium (DMEM) supplemented with 10% fetal bovine serum (10% FBS-DMEM) was added to each well. The plates were incubated in a humidified 37° C., 5% $CO_2$ incubator and the microvascular networks in these cultured microvessel constructs were allowed to develop within the culture well for seven to ten days.

Human fat microvessel fragments (HFMF) were also isolated and cultured microvessel constructs were prepared from human abdominoplasty following this procedure. HFMF can also be isolated from liposuction fat according to this procedure except that 4 mg/mL collagenase is used in the enzymatic disruption step.

The person of ordinary skill will understand that freshly isolated microvessel constructs may also be produced following this procedure, except that the constructs are not incubated for 7–10 days in an incubator. In order to get a solidified collagen gel construct, however, freshly isolated microvessel constructs would typically be incubated at a temperature sufficient to allow polymerization of the collagen.

The skilled artisan will appreciate that other enzymes, such as dispase, trypsin, elastase, liberase, or the like, may be used in such digestion steps in place of collagenase. The skilled artisan will also understand that many such digestive enzyme preparations will vary in activity from vendor to vendor and from lot to lot (see, e.g., London et al., Diabetes & Metabolism, 23:200–07, 1998). For example, a given enzyme lot might have a high specific activity such that its use at the identified conditions will result in RFMF preparations that consist of an unacceptably low number of microvessel fragments due to over-digestion of the preparation. Further, certain enzyme preparations reportedly contain various contaminants that may be harmful to tissues, such as endotoxins and additional contaminating proteases (see, e.g., Arita et al., Pancreas 23:62–67, 2001). Thus, the person of ordinary skill understands that one routinely titrates each enzyme lot in a standard assay to determine its comparative enzyme activity prior to use.

Example 3

Implantation of Prevascularized Constructs to Revascularize Ischemic Heart Tissue Prevascularized constructs comprising RFMF were prepared essentially as described in Example 2, above. Cultured microvessel constructs were cultured in 48-well plates with 10% FBS-DMEM for seven days in a humidified 37° C., 5% $CO_2$ incubator prior to implantation. During this culture period the microvessels formed an extensive microvessel network throughout the three-dimensional culture (see FIG. 1). Freshly isolated microvessel constructs were prepared and then immediately implanted.

To demonstrate the revascularization of ischemic myocardium, a cryoinjury model of infarction was used to generate infracted cardiac tissue. Male retired breeder Fischer 344 rats were used for the epicardial implantation of the prevascularized constructs. Epicardial access was gained through a lateral thoracotomy and cryoinjury was achieved by administration of a metal probe that had been cooled in liquid nitrogen on the anterior free wall of the left ventricle. Following infarct formation, prevascularized constructs, either freshly isolated microvessel constructs or cultured microvessel constructs, were attached directly to the epicardial surface, over the site of induced injury, using two 8-0 sutures. Control rats received infarct only, or infarct followed by the implantation of a three-dimensional culture lacking RFMF. The chest was closed in layers and the animals recovered. The animals were sacrificed and their hearts were excised 14 days post-implantation.

Tissue sections were fixed in HISTOCHOICE™ (Amresco, Solon, Ohio) and paraffin embedded for histology and immunochemistry according to conventional methods. Six micron sections were cut for standard H&E staining as well as for endothelial cell identification using the GS-1 lectin (*Griffonia simplicifolia*). H&E staining confirmed the presence of a mature, patent vasculature comprised of arterioles, venules and capillaries throughout both the explanted freshly isolated microvessel constructs and the explanted cultured microvessel constructs.

Gross observation of the explanted prevascularized constructs revealed the presence of microvessels within them by 14 days post-implantation. The constructs were well integrated with the epicardial surface and vascularization was seen throughout both the freshly isolated microvessel constructs and the cultured microvessel constructs. The presence of red blood cells within vessel walls was noted throughout the prevascularized constructs, demonstrating that the implanted prevascularized constructs rapidly inosculated with the underlying epicardial vasculature. Control implants remained avascular. Epicardial Vascular Densities were higher in the animals receiving prevascularized constructs than animals receiving control constructs.

The skilled artisan will understand that prevascularized constructs can be combined with tissues or organs by implanting the constructs at appropriate anatomical sites, following similar procedures. For example, prevascularized constructs may be combined with damaged or diseased tissues or organs in need of revascularization, by placing the constructs on the surface of, within, adjacent to, or on an external layer of the damaged or diseased tissue or organ. The skilled artisan will also understand that prevascularized constructs can be combined with tissues, organs, or engineered tissues by injection into, or adjacent to, a damaged or diseased tissues or organs or engineered tissue, for example, a syringe with a needle of an appropriate gauge to allow the microvessel fragments and additional cell types (if present) to pass through without being damaged.

Example 4

Implantation and Evaluation of Cultured Microvessel Constructs

Figure 4:
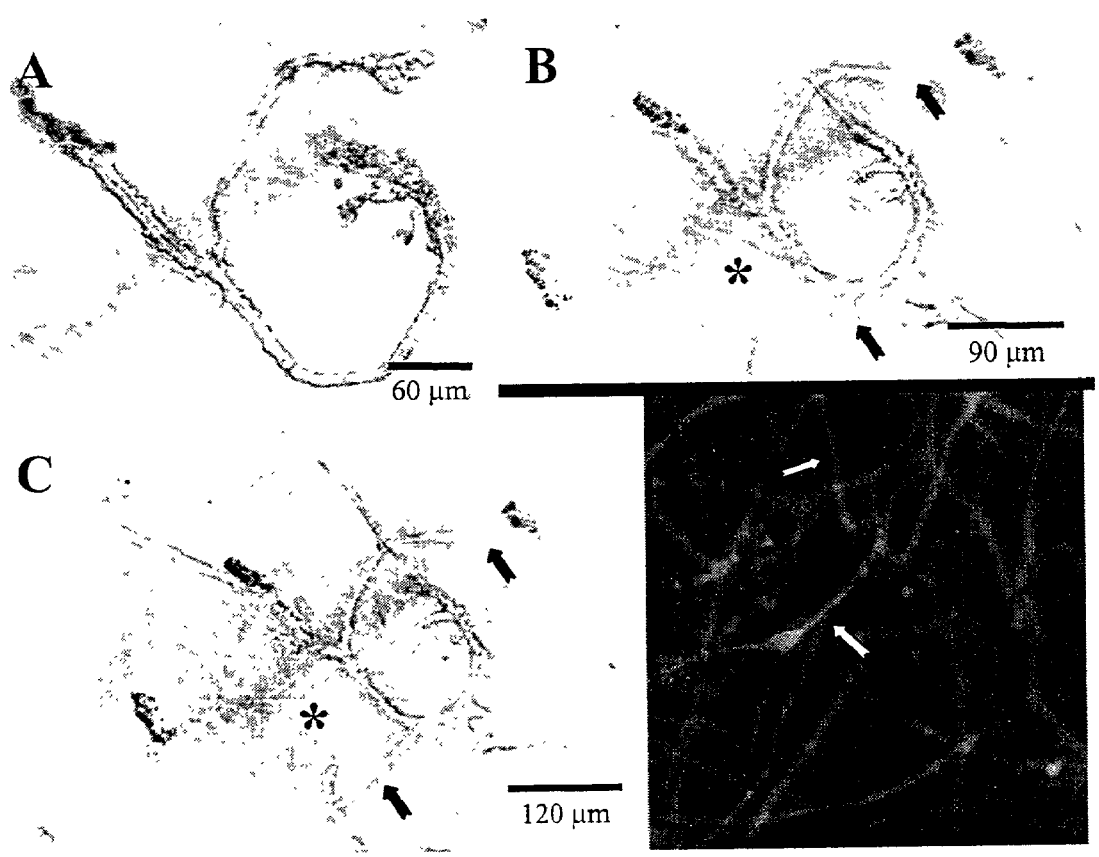
FIG. 4. Vessel fragments exhibit features of angiogenesis when cultured in 3-D collagen gels. A A freshly isolated arteriole fragment with a capillary branch suspended in the collagen gel (day 0). B, C The same vessel fragment shown in A at day 4 (B) and day 5 (C) of culturing. Multiple sprouts are present by day 4 some which may continue to elongate (arrow) or regress (*) by the next day. D A representative field of neovessels (arrows) stained by immunofluorescence that have formed within the collagen gel system by day 11 of culturing.

Cultured microvessel constructs, comprising RFMF, such as described in Example 2 were cultured for 7–11 days. During the first 5 days of culture prior to implantation, angiogenic sprouts were observed on individual fragments in the prevascularized constructs. These sprouts were seen to undergo a dynamic process of growth resulting in a loose collection of elongated, simple microvessels by day 11 (FIG. 4). The cultured prevascularized constructs and control constructs lacking microvessel fragments ("control constructs") were implanted in the subcutaneous position on the flanks of SCID (Severe Combined Immuno-Deficient) mice for 1, 3, 5, 7, 10, 14, 21, 28, or 35 days or for 4 months. Each mouse received two implants, a prevascularized construct on one side and a control construct on the other.

At the time of explant, implants were observed for the presence of blood-containing vasculature and photographed. Explants were fixed in 2% paraformaldehyde/PBS and paraffin embedded for histology. General histological structure was determined on 6 μm thick sections with hematoxylin and eosin (H&E) staining and the vasculature identified using a rodent-specific lectin, GS1 (*Griffonia simplicifolia*).

Figure 5:
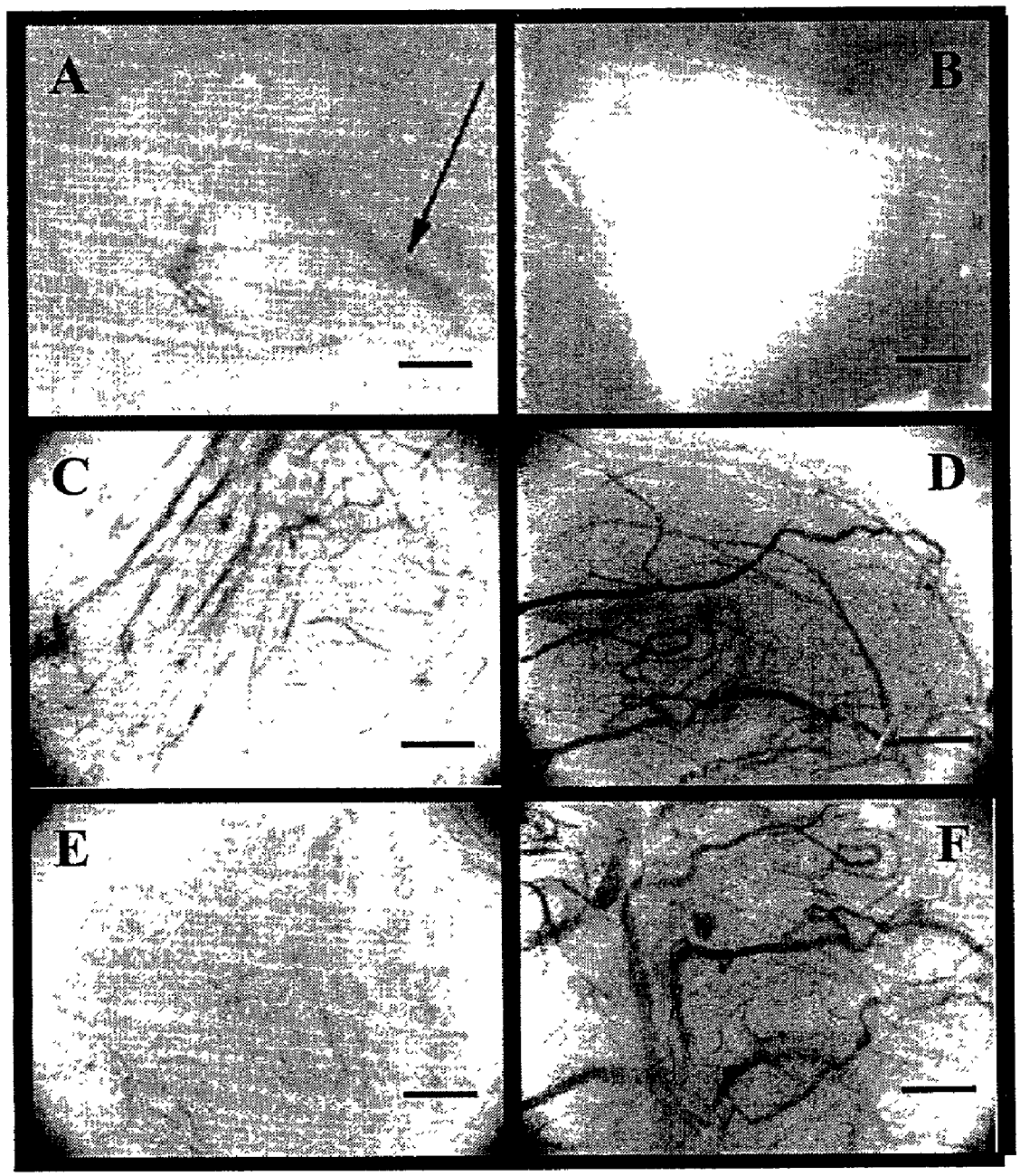
FIG. 5. Collagen gels containing cultured neovessels (prevascularized construct) inosculate with the host vasculature and carry blood when implanted into scid/scid mice. A,B Gross views of a prevascularized construct (A) and an avascular collagen gel (B) 7 days and 3 days post-implantation, respectively. The long arrow in A points to a large vessel entering the construct from the surrounding host tissue. C-F Orthogonal Polarized Spectroscopy (OPS) images of separate prevascularized implants at day 3 (C), day 7 (D), and day 14 (F) or a day 7, avascular control gel (E). OPS detects the presence of hemoglobin.
Figure 6:
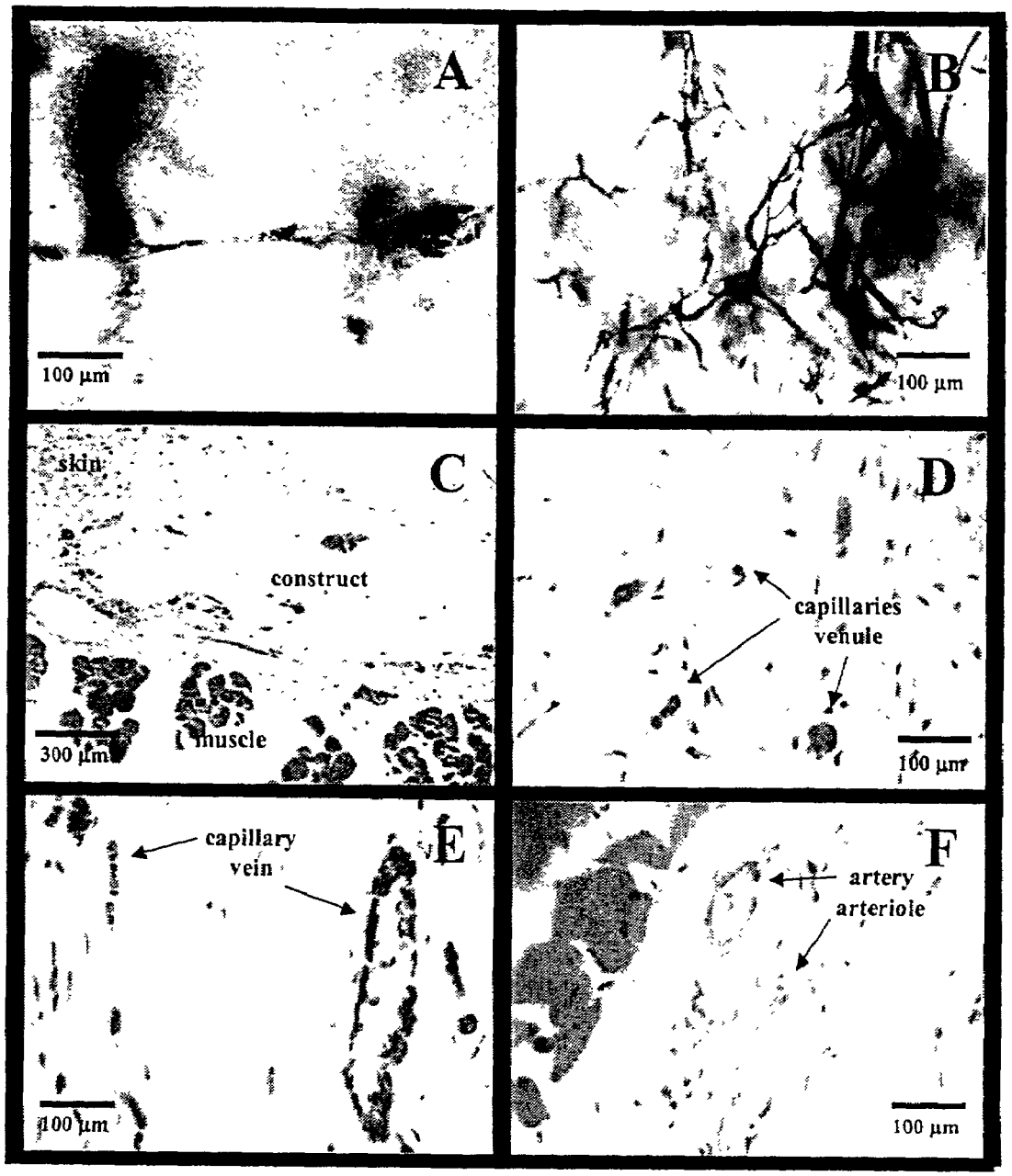
FIG. 6. Histology of characteristic prevascularized constructs after 1 day (A), 2 days (B) and 14 days (C-F) of subcutaneous implantation. (A-B) Constructs were perfusion-filled with ink to identify those vessels within the construct connected to host vessels. (C-F) Red blood cells are present within vessel-like compartments in all sections. By day 14 capillaries, veins and arteries are present within the construct.

In contrast to the implanted control constructs, the implanted prevascularized constructs were associated with superficial, blood-filled vessels (FIG. 5). Orthogonal polarized spectral (OPS) imaging, which selectively detects hemoglobin, revealed blood-containing vessel structures throughout the constructs as early as 3 days post-implantation (FIG. 5). Between days 3 to 14 post-implantation, the simple network was observed to remodel into a more typical appearing vasculature with vessels of various dimensions and orientations present throughout the implant (FIG. 5). This mature vessel architecture was observed to be established by day 7 and persisted through at least day 35. Only surface blood due to the dissection was detected on implanted control constructs with OPS (FIG. 5). Histology of explanted, prevascularized constructs (FIG. 6) confirmed the presence of blood in the vessels and the heterogeneous, more mature vascular network indicated by the OPS imaging. A full range of vessel types commonly seen in a mature, functional vascular bed was observed, including small arteries, arterioles, capillaries, venules and veins (FIG. 6). Based on the histology, it was evident that blood filled vessels were present in implants as early as day 1 post-implantation (FIG. 6). However, vessel perfusion was limited to the implant periphery, adjacent to host tissues.

Figure 7:
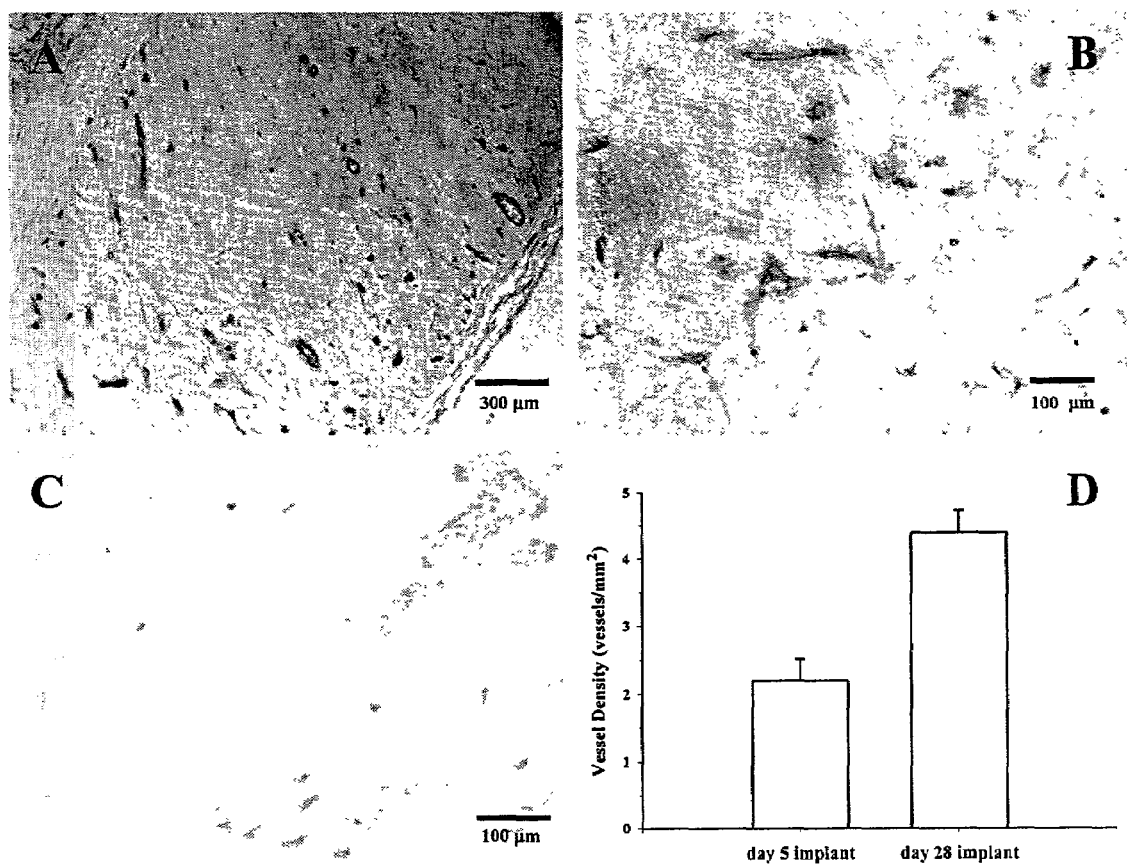
FIG. 7. Prevascularized implants contain vascular endothelium are exhibit little inflammation. A-B Sections of either day 5 (A) or day 28 (B) implants stained for the rodent-specific endothelial cell marker, GS-1. C A section of day 5 implant stained for the presence of infiltrating macrophages (arrow). D Vessel density measurements counted from GS-1 stained sections of implanted prevascularized constructs. Vessel density increases in implanted constructs between day 5 and day 28 post-implantation.

Staining for an endothelial specific marker with the lectin GS-1 verified the vascular nature of the vessels (FIG. 7) as well as revealed a limited number of non-vascular, single cells (GS-1 negative) dispersed throughout the implant (FIG. 7). These dispersed, single cells were of rat origin (see below) and thus were part of the original isolate used to form the prevascularized construct. Control constructs were found to be void of vessels or cells. Histology sections of implants stained for the presence of macrophages revealed limited inflammatory cell infiltration into the implant (FIG. 7).

Since the prevascularized constructs comprising RFMF from male rats were implanted in female SCID mice, it was possible to determine by PCR if the vessels within the prevascularized construct were derived from the implanted cultured microvessel construct or due to the ingrowth of host, mouse vessels. Rat genomic DNA was isolated from rat-tail tissue, rat Y chromosome DNA was synthesized by PCR (F: ggt tct aga ctg taa aac cca gac R: act taa aac taa gct tat tgg cca) and labeled with biotin (Vector Laboratories). Eight micron explant sections were deparaffinized in xylene, rehydrated in an ethanol series, treated with 0.2 M HCl, followed by an incubation in 0.1% TritonX-100 for 2 min and finally treated with 10 ug/ml of proteinase K in PBS. Following post-fixation with 4% paraformaldehyde, chromosomal DNA was released by treatment with 0.1 M TEA, 0.25M acetic anhydride and washed 2 times in 2× SSC. Sections were dehydrated in ethanol from 50% to 100% and hybridized.

A biotin-labeled DNA probe, specific to a repeat element of the rat Y chromosome (Essers et al., Cytogenet. Cell. Genet. 69:246–252, 1995), was used to analyze sections from day 5 and day 28 implants. Sections were pre-hybridized in 50% formamide, 20% dextran sulfate in 2× SSC, and salmon sperm DNA for 20 minutes at 55°. This Y-chromosome probe was denatured at 95° C. for 5 minutes and was incubated overnight in pre-hybridization solution at 42° C. The hybridized sections were washed twice for five minutes with 4× SSC 5 minutes at room temperature, for 20 minutes in 2× SSC at room temperature, for 15 minutes in 0.2× SSC at 42° C., and for 15 minutes in 0.1× SSC at 42° C. The hybridized labeled probe was detected via an enzyme-conjugated StrepAvidin according to manufacturer's instructions (Vector Laboratories).

Figure 8:
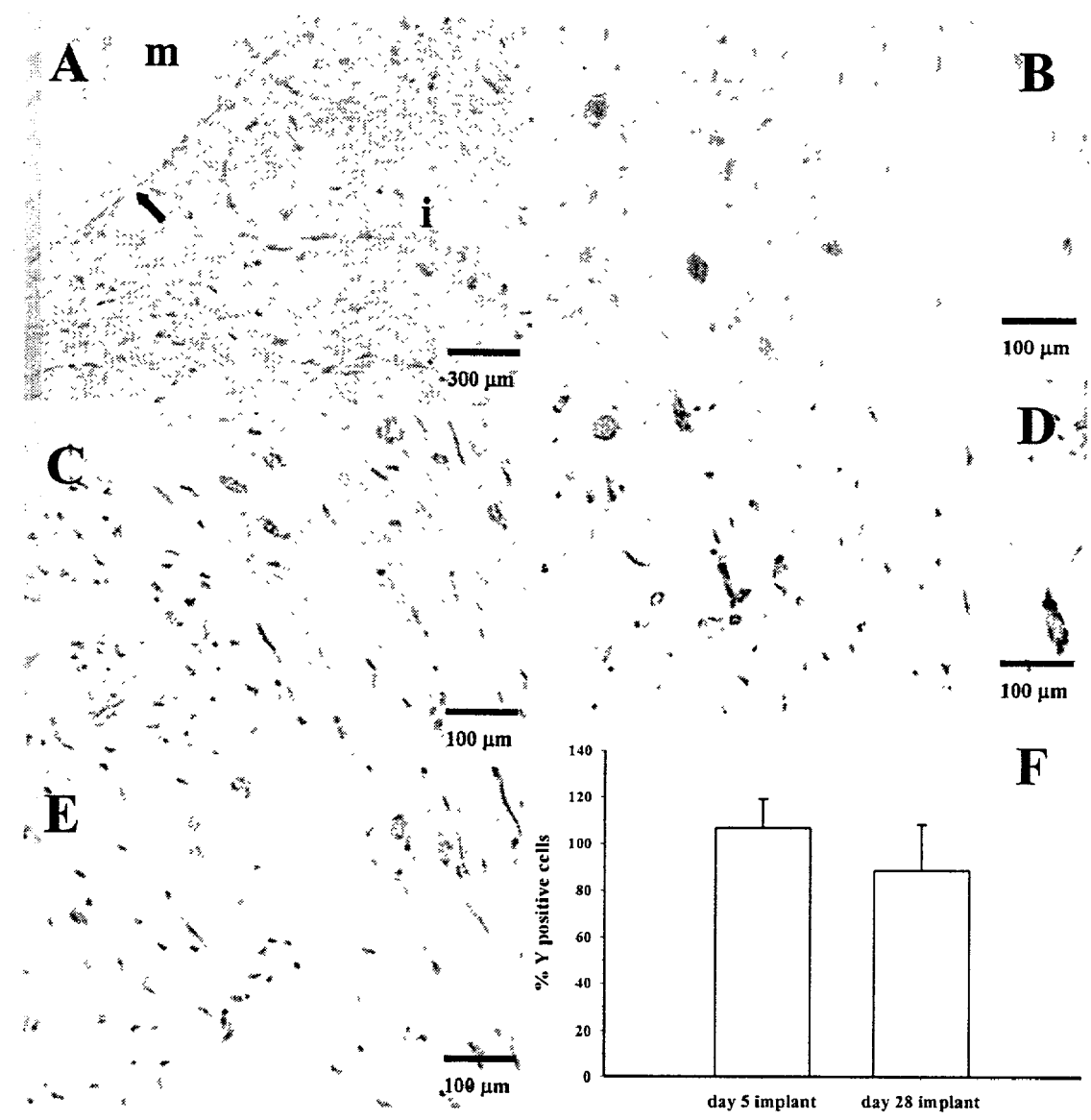
FIG. 8. Nearly all of the cells within the prevascularized constructs are derived from the original cultured isolates. Serial sections of day 5 (B,D) and day 28 (A,C,E) implants were either stained with hematoxylin to identify all nuclei within the section or labeled by in situ hybridization using a probe for the Y chromosome to identify cells from the original isolate (vessel fragments were isolated from male rats and constructs implanted into female mice). A A low magnification of a day 28 implant labeled by in situ hybridization. The "m" depicts the underlying host (mouse) musculature, while the "i" demarks the implant. F For each serial section pair, the number of Y chromosome-positive nuclei were compared to the total number of nuclei (counted from the hematoxylin-stained sections) and reported as % Y positive nuclei in each section for day 5 and day 28 implants.

As seen in FIG. 8, vessel-like structures and single cells throughout the implant were detected with the Y chromosome-specific probe. Cells within the implants at day 5 and day 28 were predominately Y chromosome-positive cells (FIG. 8). No Y-positive cells were observed within the underlying muscle of the host mouse (FIG. 8).

Figure 9:
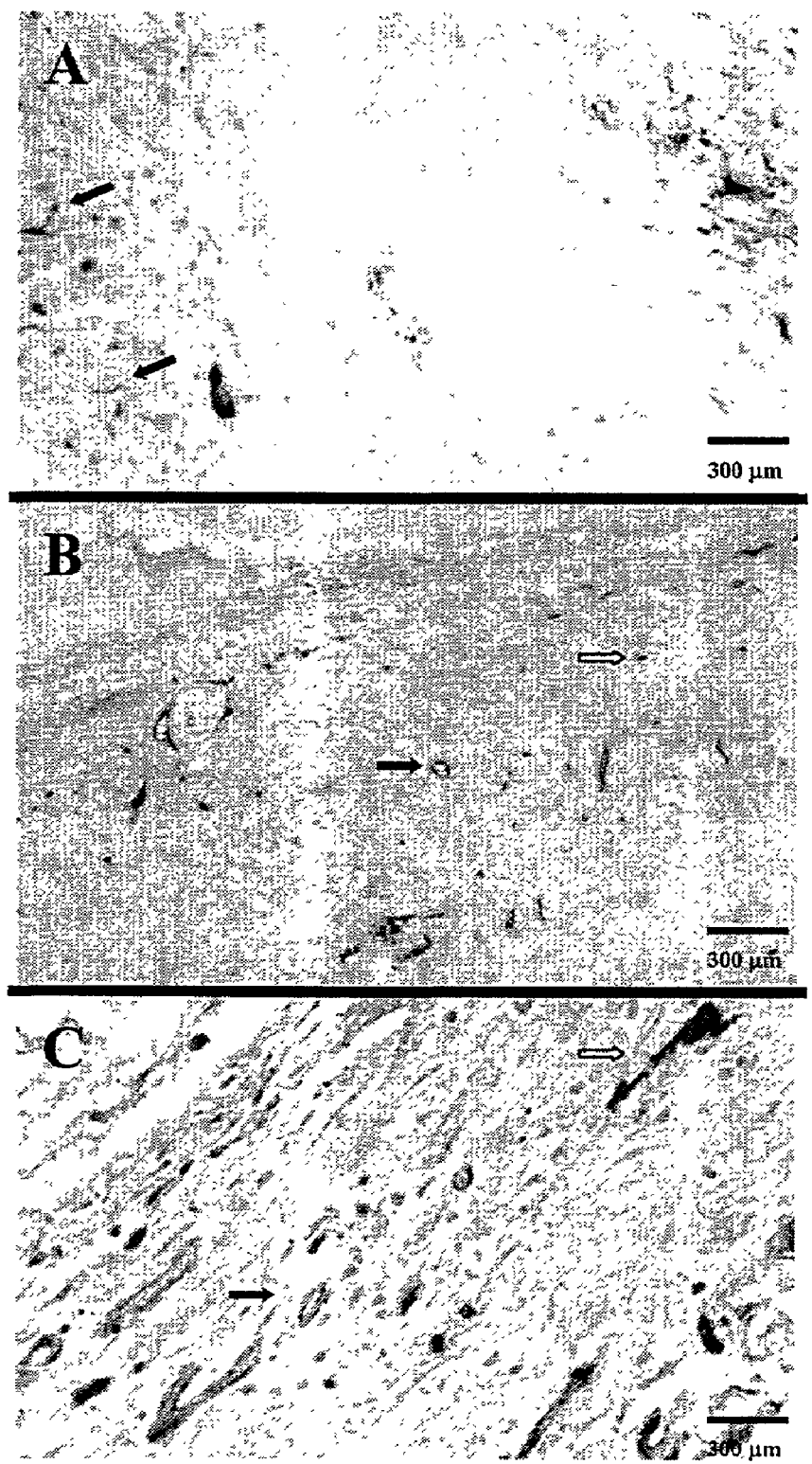
FIG. 9. Collagen gel implants that are vascularized by freshly isolated human microvessel fragments are not replaced by host vasculature by day 28 post-implantation. A A section of a human vascularized construct stained with the rodent specific, vascular marker GS-1. The lectin labels vessels within the surrounding mouse tissue (arrows), but only limited numbers of vessels within the construct (large clear zone in the center of the section). In contrast, the human-specific lectin, UEA1 labels only vessels (open and closed arrows) within the construct (A, low mag.; B, high mag.), but not within the surrounding host tissue.

Freshly isolated microvessel constructs were also prepared using RFMF, as described in Example 2, and implanted subcutaneously into the flanks of female scid/scid mice, as described above. As with cultured microvessel constructs, the freshly isolated microvessel constructs developed a recognizable, blood-filled vasculature (FIG. 9). Freshly isolated microvessel constructs were also prepared as described in Example 2, except that human microvessel fragments isolated from abdominoplasty tissues were used instead of RFM F. These constructs were implanted subcutaneously into the flanks of female scid/scid mice, as described above. As with the RFMF microvessel constructs, implanted prevascularized constructs comprising human microvessel fragments were well perfused by day 7 post-implantation. Histology sections of these explanted constructs were probed with the human endothelial cell-specific lectin, UAE (Ulex Europaeus Agglutinin I), to verify the human origin of the implant vasculature (FIG. 9).

Example 5

Isolation of Human Stem Cells from Liposuction Fat

Multilineage progenitor cells, believed to be stem cells, are isolated from human adipose tissue, essentially as described by Zuk et al. (see also Hauner et al., J. Clin. Endocrinol. Metabol. 64:832, 1987; Katz et al., Clin. Plast.

Surg. 26:587, 1999). Human adipose tissue is obtained from a liposuction procedure using a hollow blunt-tipped cannula introduced into the subcutaneous space through small incisions of approximately 1 centimeter (cm). The cannula is attached to gentle suction and moved through the adipose compartment to mechanically disrupt the fat tissue. A solution of saline and the vasoconstrictor epinephrine is infused into the adipose compartment to minimize blood loss and contamination of the fat tissue by peripheral blood cells. Approximately 300 cubic centimeters (cc) of the lipoaspirate is extensively washed with equal volumes of PBS and the washed lipoaspirate is digested using a 0.075% collagenase solution for 30 minutes at 37° C. Enzyme activity is neutralized using 10% FBS-DMEM and the preparation is centrifuged at 1200× g to obtain the high density pellet, referred to as the stromal vascular fraction (SVF). Contaminating red blood cells are lysed by resuspending the SFV pellet in 160 mM $NH_4Cl$ and incubating the mixture at room temperature for ten minutes. The treated SFV is centrifuged at 1200× g and the resuspended pellet is filtered through a 100 µm nylon mesh to remove cellular debris. The SFV is suspended in 10% FBS-DMEM supplemented with 1% antibiotic/antimycotic solution, plated into multi-well plates, and incubated in a humidified incubator at 37° C. and 5% $CO_2$. Following overnight incubation, the plates are washed extensively with PBS to remove nonadherent red cells. The resulting processed lipoaspirate (PLA) can reportedly be maintained in 10% FBS-DMEM in a 5% $CO_2$ incubator at 37° C. for at least 13 passages (165 days in culture) without a significant loss in population doubling over time.

Reportedly, cells in this PLA undergoes lineage-specific differentiation under appropriate conditions in vitro, as described by Zuk et al. This multilineage potential reportedly includes adipogenic, osteogenic, chondrogenic, and myogenic lineages. Thus, the skilled artisan will appreciate that PLA is a readily available source of multilineage cells, presumably stem cells, that would be appropriate for inclusion in prevascularized constructs for combining with a variety of organs and tissues, including engineered tissues. PLA cells can be incorporated into prevascularized constructs by mixing them into the three-dimensional culture environment along with microvessel fragments, following, for example, the procedure described in Example 2 above. In addition, PLA can be implanted in parallel with, or in addition to, the prevascularized constructs. Once in the appropriate environment in vivo, the multilineage/stem cells in PLA will differentiate into the appropriate lineage to allow repopulation or reconstruction of damaged or dysfunctional tissue or organs in need of revascularization.

The skilled artisan will understand that the same liposuction preparation may be used to isolate both microvessel fragments and PLA and that these cells may be for used in preparing freshly isolated microvessel constructs or cultured microvessel constructs. Further, an autologous construct can be prepared using, for example, but without limitation, PLA and microvessel fragments obtained from the patient's lipoaspirate and a fibrin-based scaffold derived from the patient's blood.

The skilled artisan will also understand that stem cells from numerous other sources may be used in various embodiments of the invention in an analogous fashion to that described in this example. For example, but not limited to, embryonic stem cells and mesenchymal stem cells obtained from bone marrow aspirate according to conventional techniques (e.g., Liechty et al., Nature Medicine 6(11):1282–1286, 2000) or from commercially available sources (e.g., Clonetics, Walkersville, Md.).

The skilled artisan will appreciate that the effective concentration of each additional cell type (e.g., stem cells, stromal cells, Relevant Cells) within the prevascularized construct is dependent on the cell type and the intended use of the prevascularized construct. Thus, the person of ordinary skill will understand that it is routine to titrate each cell type in test prevascularized constructs to identify the effective concentration for a particular use. For example, to determine the effective concentration of PLA-derived human stem cells in prevascularized constructs, test constructs prepared according the method of Example 2 could be prepared as follows. Eighteen parallel liquid three-dimensional culture preparations comprising 13,000 human microvessel fragments each and either 0, 10, 100, 1000, 10000, or 50,000 PLA-derived human stem cells/ml are prepared in six triplicate sets, and allowed to polymerize. The 18 parallel constructs are combined with target tissues or organs by implanting the constructs directly into test animals, as described in Examples 3 and 4. After an appropriate implantation period, the prevascularized constructs would be explanted and the recipient animal, the implant, and the relevant tissue or organ would be evaluated, as described in Examples 3 and 4. To evaluate the effect of the additional cell type(s) on the proliferation and growth microvessel fragments in cultured microvessel constructs, similar triplicate constructs could also be incubated, for example in a humidified 37° C., 5% $CO_2$ incubator, and evaluated over a seven to ten day period, as described in Example 4.

The skilled artisan will understand that further refinement of the appropriate number of additional cells for a particular prevascularized construct can be determined by additional experiments, based on the results of the above procedure. For example, if in the first experiment that 1000 additional cells/ml demonstrated the best results, additional tests using 500, 2000 and 6000 cells/ml would allow further refinement of the optimal number of additional cells per construct. A similar procedure could be followed to determine the appropriate concentration of any stem cell, stromal cell, Relevant Cell, genetically engineered cell, or combinations thereof, in a prevascularized construct.

Example 6

Isolation of Human Microvessel Endothelial Cells from Liposuction Fat

Liposuction fat was procured from the procedure site and transported in medium, for example, M199. The fat in M199 was poured over a sterile sieve with a 500 micron pore size and the retentate was washed with DCF-PBS to remove red blood cells. Approximately 10 grams (about 10 mLs) of the washed liposuction fat was transferred to a sterile 50 mL polycarbonate Erlenmeyer flask containing a TEFLON® coated stir bar and ten mLs of sterile collagenase solution (4 mg/ml collagenase Pure 1 (Worthington Biochemicals) and 4 mg/ml human serum albumin in DCF-PBS) was added. The flask was stirred at approximately 64 revolutions per minute for 30 minutes in a Dubnoff water bath 37° C. to digest the fat. The digested solution was transferred to 15 mL polypropylene conical centrifuge tubes and centrifuged for four minutes at 700× g. The endothelial cells and red blood cells pelleted, the fat formed a "plug" at the top of the tube with the collagenase solution supernatant was between them.

The fat and supernatant were discarded, the cell pellet was resuspended in approximately 2 mLs DCF-PBS supplemented with 0.1% BSA, and then transferred into clean 15 mL conical centrifuge tubes, taking care that the transfer of fat was avoided. The tubes were centrifuged at 700× g for three minutes at room temperature. The supernatant was poured off and the endothelial cell preparation was resuspended in sodding medium (M199 supplemented with between 0.1% and 1% EFAFBSA). (See also, Stopeck et al., Cell Transplant. 6:1–8, 1997; Hoying et al., J. Cell. Physio. 168:294–304, 1996).

Example 7

Generation of Genetically Engineered Endothelial Cells for Incorporation into Prevascularized Constructs Human endothelial cells are genetically engineered to generate cells that constitutively express human gamma interferon (γ-IFN), essentially as described by Stopeck et al., Cell Transplantation 6:1–8,1997. The human endothelial cell pellet from Example 6 is resuspended in M199 supplemented with 20% heat-inactivated FBS, 5 mM HEPES, 1.7 mM L-glutamine, and 60 μg/mL endothelial cell growth supplement (Jarrell et al., J. Vasc. Surg. 1:757–64,1984) containing 25 μg/mL heparin and plated on gelatin coated polystyrene T-25 tissue culture flasks and incubated in a conventional humidified 37° C., 5% $CO_2$ incubator and maintained in culture.

Supernatants of high titer ($1\times10^6$–$1\times10^7$ cfu/mL) recombinant retrovirus containing either the *E. coli* beta-galactosidase (β-gal) or human γ-IFN gene were obtained from Viagene, Inc. (San Diego, Calif.). These recombinant retroviruses comprise a Moloney murine leukemia virus genome with viral structural genes replaced by either the β-gal or the human γ-IFN gene. T-25 flasks of human endothelial cells at 30–40% confluency are transduced for 6–18 hours on 2 consecutive days with media containing 750 μg/mL protamine sulfate and retrovirus supernatants at a multiplicity of infection of 5.

Forty-eight hours after transduction, cells are fixed with 2% formaldehyde prior to staining with X-gal solution (5 mM potassium ferricyanide, 5 mM potassium ferrocyanide, 2 mM MgCl2, and 1 mg/,L X-gal (Sigma, St. Louis, Mo.) in PBS overnight at 37° C. The transduction efficiency is calculated as the number of cells staining positive for β-gal divided by the total number of cells counted. β-gal transduced or human γ-IFN transduced endothelial cells are selected using 1 mg/mL G418 (Gibco BRL) selection medium.

Total RNA is extracted from transduced and control endothelial cells using Trizol (Gibco BRL) for RT-PCR analysis, as described. Human endothelial cells transduced according to this procedure reportedly produce 80–130 pg/mL of human γ-IFN per $10^5$ cells after 24 hours in culture (see Stopeck et al., Cell Transplantation 6:1–8, 1997 and U.S. Pat. No. 5,957,972).

The skilled artisan will understand that replacement of the human γ-IFN or γ-gal gene in these recombinant retrovirus vectors with alternate genes of interest requires only routine manipulation using techniques generally known in the art. Thus, any number of genes of interest may be transduced into and expressed by endothelial cells following this exemplary technique. The skilled artisan will also understand that, following techniques generally known in the art, a variety of mammalian cells can routinely be transduced or transfected to express virtually any gene product of interest (see, e.g., Twyman, Advanced Molecular Biology: A Concise Reference, Bios Scientific Publishers, Springer Verlag New York, particularly Chapter 24). Particularly useful gene products of interest include, for example, but without limitation, cytokines, insulin, human growth hormone, plasminogen activator, soluble CD-4, Factor VIII, Factor IX, von Willebrand Factor, urokinase, hirudin, interferons, including alpha-, beta- and gamma-interferon, tumor necrosis factor, interleukins, hematopoietic growth factor, antibodies, glucocerebrosidase, adenosine deaminase, phenylalanine hydroxylase, human growth hormone, insulin, erythropoietin, VEGF, angiopoietin, hepatocyte growth factor, PLGF, and other proteins or gene products appropriate for local or systemic delivery, particularly blood-borne delivery.

Genetically engineered cells, particularly genetically engineered endothelial cells, may be incorporated into the prevascularized constructs of the invention at appropriate concentrations, as described. Prevascularized constructs comprising autologous microvessel fragments in an autologous three-dimensional culture matrix and genetically engineered cells prepared from autologous endothelial cells are particularly useful for certain applications. The skilled artisan that a wide variety of techniques may be used to genetically modify cells, i.e., transferring genes and nucleic acids of interest into recipient cells, using techniques generally known in the art, including, but not limited to: transfection (e.g., the uptakeof naked nucleic acid), for example, but not limited to polyethylene glycol transfection, chemical transfection (e.g., using calcium phosphate and DEAE dextran), lipofection, electroporation, direct injection, and microballistics; and transduction, using a number of viral vectors, such as, without limitation, adenovirus vectors, herpesvirus vectors, retrovirus vectors, including, but not limited to lentivirus vectors. Descriptions of such techniques may be found in, among other places, Ausubel et al., Current Protocols in Molecular Biology (including supplements through March 2002), John Wiley & Sons, New York, N.Y., 1989; Sambrook et al., Molecular Cloning: A Laboratory Manual, $2^{nd}$ Ed., Cold Spring Harbor Laboratory Press, Cold Spring Harbor, N.Y., 1989; Sambrook and Russell, Molecular Cloning: A Laboratory Manual, $3^{rd}$ Ed., Cold Spring Harbor Laboratory Press, Cold Spring Harbor, N.Y., 2001; Beaucage et al., Current Protocols in Nucleic Acid Chemistry, John Wiley & Sons, New York, N.Y., 2000 (including supplements through March 2002); Short Protocols in Molecular Biology, $4^{th}$ Ed., Ausbel, Brent, and Moore, eds., John Wiley & Sons, New York, N.Y., 1999; Davis et al., Basic Methods in Molecular Biology, McGraw Hill Professional Publishing, 1995; Molecular Biology Protocols (see the highveld.com website), Protocol Online (protocolonline.net); and Twyman, Advanced Molecular Biology: A Concise Reference, Bios Scientific Publishers, Springer-Verlag New York.

Example 8

Isolation of Pancreatic Islets

Human pancreatic islets are isolated using the tube method of ductal canulation and collagenase infusion, essentially as described by Arita et al., Transplantation 68(5): 705–07, 1999. A polyethylene tube (INTRAMEDIC, Clay Adams, Parsippany, N.J.) with a tight-fitted injection needle on one end, a diameter of approximately 0.64 to 1.47 millimeters (mm) depending on the duct size, and of a length similar to the pancreas is used. The tube is inserted into the main duct of a whole pancreas, starting from the head and extending to the tail, and the duct is ligated around the tube.

The pancreas is infused and digested with approximately 150–300 mL collagenase solution (3 mL/g pancreas weight), comprising 2–2.3 mg/mL of lots 9 or 522 collagenase P (Boehringer Mannheim, Indianapolis, Ind.). The collagenase-infused pancreas is chopped into small pieces, placed in a digestion chamber with remaining collagenase solution and gently agitated in a 37° C. water bath. Total incubation time in collagenase is 15 minutes. The collagenase solution is replaced by cold LAP-1 preservation solution (Islet Technology, North Oaks, MN) and the digestion chamber is placed in an ice-water bath and gently agitated. The supernatant, containing islets and fragmented acinar and duct tissue, is decanted every 5–10 minutes into collection bottles containing LAP-1 solution and fetal bovine serum. Fresh LAP-1 solution is added to the digestion chamber and cold digestion continues until most of the islets are released, approximately 30–40 minutes. The digested tissues are collected and islets are purified by centrifugation on a discontinuous three-layer gradient of Euro-Ficoll solution using a COBE2991 cell processor (COBE Laboratories, Lakewood, Colo.).

Numerous other islet purification techniques, generally known in the art, may also be employed. Exemplary islet purification techniques may be found in, among other places, London et al., in Methods in Cell Transplantation, Ricordi, ed., at pages 439–54, 1995; Lakey et al., Transplantation 72:562–63, 2001; Olack et al., Human Immunol. 60:1303–09,1999; London et al., Diabetes Metab. 24:200–07, 1998; Linetsky et al., Diabetes 46:1120–23, 1997; Arita et al., Pancreas 23:62–67, 2001; and Wang et al., Nat. Biotechnol. 15:358–62, 1997. The person of ordinary skill in the art will understand that such isolated pancreatic islets may be useful as Relevant Cells in, for example, prevascularized constructs for revascularizing a damaged or diseased pancreas.

Example 9

Isolation of other Relevant Cells

Cells from animal or human liver are obtained as described by Macdonald et al. in Atala et al., Chapter 11, particularly at pages 155–166. Human adipocytes are obtained according to the method of Katz, as described in Atala et al., Chapter 20. Human smooth muscle cells are isolated according to the method of Kim et al., as described in Atala et al., Chapter 21. Human and animal cardiomyocytes are obtained using the method of Soker et al., as described in Atala et al., Chapter 22 or Sakai et al., Cardiovascular Research Institute, American Heart Association, 1999, at pages 108–14 (see also Tomita et al, Id. at pages 92–101 (describing the use of bone marrow cells that differentiate into cardiomyocytes) and Atkins et al., J. of Heart and Lung Transplantation, 1999, at pages 1173–80 (describing cellular cardiomyoplasty using autologous skeletal myoblasts)). Myocytes, fibroblasts and satellite cells are obtained from animal or human striated muscle following the methods of Kosnick et al., as described in Atala et al., Chapter 23. Myoblasts are isolated and cultured according to the methods of Atkins et al., as described in J. of Heart and Lung Transplantation, 1999, at pages 1173–80. Chondrocytes from human or animal articular cartilage are obtained according to the methods of Kinner et al., as described in Atala et al., Chapter 25. Mouse and rat bone marrow cells are obtained from femoral marrow and human bone marrow cells are obtained from bone marrow aspirates or trabecular bone biopsies using the methods of Davies et al., as described in Atala et al., Chapter 26.

Relevant Cells isolated according to these or other conventional methods known in the art may be used in preparing prevascularized constructs of the invention. The skilled artisan will understand that in certain embodiments, suspensions of such Relevant Cells may be added to liquid three-dimensional cultures in addition to microvessel fragments to generate prevascularized constructs. In certain embodiments, such Relevant Cells, the microvessel fragments, or both, are resuspended in a liquid three-dimensional culture matrix. Alternatively, such Relevant Cells can be added to a scaffold or other preformed matrix before, after, or simultaneously with the microvessel fragments to form prevascularized construct according to the invention. These prevascularized constructs can then either be directly combined or cultured and then combined according to the methods disclosed herein, depending on whether freshly isolated microvessel constructs or cultured microvessel constructs are desired.

The person of ordinary skill will appreciate that prevascularized constructs may be prepared using Relevant Cells and microvessel fragments isolated from any mammalian species following the methods described herein. For example, rat prevascularized constructs can be prepared using rat microvessel fragments in an appropriate three dimensional culture matrix, with or without appropriate rat stem cells, rat stromal cells, rat hepatocytes, rat myocytes, etc. Similarly, a rabbit prevascularized construct would comprise rabbit microvessel fragments, an appropriate three dimensional matrix, and optionally rabbit stem cells, rabbit stromal cells, rabbit hepatocytes, rabbit myocytes, etc.; and so forth. Such prevascularized constructs are then combined with organs or tissues, including engineered tissues, according to the methods of the invention.

Example 10

Preparation of Prevascularized Constructs using Fibrin-Derived Scaffolds

Three hundred milligrams of fibrinogen powder is dissolved in 10 mL HEPES-buffered saline solution (30 mg/mL) and passed through a 0.2-micron syringe filter (fibrinogen solution). Two hundred and fifty units of thrombin powder is dissolved in 10 ml of HEPES-buffered saline (25 units/mL) and filtered through a 0.20-micron syringe filter (thrombin solution). The fibrinogen solution is diluted using Medium 199 (M199) supplemented with 12% FBS to yield a diluted fibrinogen solution containing 5 mg/mL fibrinogen and 10% FBS. The thrombin solution is diluted with M199 containing 15 mM CaCl to yield a diluted thrombin solution with a thrombin concentration of 2.5 units/mL. Four parts diluted fibrinogen solution are mixed with one part of the diluted thrombin solution and one part cell suspension and this mixture is placed in an incubator at 37° C. to allow the fibrin to polymerize. An acellular fibrin scaffold is prepared using an equal volume of medium without cells in place of the cell suspension. The skilled artisan will appreciate that the concentration of cells or microvessel fragments in the "cell suspension" must be adjusted to achieve the desired final cell/microvessel fragment concentration, for example, approximately 11,000–15,000 microvessel fragments per m L.

An autologous fibrin-derived three-dimensional culture or scaffold is prepared using materials obtained from a recipient patient's or animal's blood as follows. Human or animal blood is collected in 9 mM buffered sodium citrate. The citrate treated blood is centrifuged for 10 minutes at 300× g and the platelet-poor plasma supernatant is decanted. Fibrin gel formation is initiated by the addition of 50 mM $CaCl_2$ and the resulting fibrin suspension is incubated at 37° C. until the fibrin polymerizes (see also, Williams et al., J. Surg. Res. 38:618–29, 1985; and Rupnick et al., J. Vascular Res. 9:788–95, 1989). The skilled artisan will understand that microvessel fragments may readily be added to the fibrin suspension prior to polymerization or to the fibrin gel. Cell types and constituents, such as drugs, cytokines, analgesics, and the like may also be added to the fibrin suspension or the fibrin gel. An allogeneic fibrin-derived three-dimensional culture may be prepared according to this Example, except that the fibrin is obtained, not from the intended recipient, but from another member of the same species. Additionally, the skilled artisan will appreciate that a fibrin suspension comprising microvessel fragments may be used in, for example, but without limitation, preparing a vascularized engineered tissue, such as in lieu of the nonpolymerized collagen solution described in Example 11.

Example 11

Preparation of a Vascularized Engineered Tissue

A suspension comprising approximately 13,000 HFMF/mL, obtained from liposuction fat according to Example 2, in the nonpolymerized collagen solution of Example 2, containing 2 ng/ml human $VEGF_{165}$ and 1 ng/ml human PDGF-BB (both from R&D Systems, Minneapolis, Minn.) is prepared. A 5 cm×7 cm piece of polyglycolic acid (PGA) felt (Albany International) with a pore size ranging from 2–15 pm and one mm thick is placed in a sterile glass pan. The suspension is gently poured into the glass pan until the felt is covered forming a prevascularized construct. The prevascularized construct is incubated at room temperature until polymerization occurs. A slice is made through the prevascularized construct along the edge of the PGA felt using a sterile scalpel.

The prevascularized construct comprising the felt is gently removed from the dish and placed directly on top of a 5 cm×7 cm piece of freshly thawed DERMAGRAFT® human fibroblast-derived dermal substitute (Advanced Tissue Sciences, La Jolla, Calif.; see Atala et al., particularly Chapter 104). The prevascularized construct is attached to the DERMAGRAFT using one suture at each corner of the prevascularized construct-engineered tissue composite. After trimming the composite to the size of a debrided foot ulcer on the leg of a human patient with diabetes, the composite is implanted into the wound bed on the patient. The composite is held securely in the wound bed using surgical dressings and a vascularized engineered tissue forms.

Alternatively, an engineered tissue, for example, but not limited to engineered pancreatic tissue prepared in a bioreactor, for example, but without limitation, according to U.S. Pat. No. 6,022,743. A flexible prevascularized construct comprising PGA felt is prepared according to this Example. The engineered pancreatic tissue is removed from the bioreactor and combined with the flexible prevascularized construct by wrapping the flexible construct around the engineered pancreatic tissue and attaching it with 8–0 sutures. The prevascularized construct-engineered pancreatic tissue combination is implanted in a human patient, following surgical following procedures. A vascularized pancreatic tissue is generated in vivo.

The skilled artisan will understand, based on these illustrative examples, that flexible prevascularized constructs may be wrapped around or within engineered tissues, such as DERMAGRAFT, and implanted into a human and cultured to generate vascularized engineered tissue. The skilled artisan will appreciate that prevascularized constructs may also be combined with an engineered tissue by placing the construct within the tissue. The combination is subsequently implanted and cultured in vivo to generate vascularized tissue. Vascularized engineered tissues may also be prepared, for example, but without limitation, combining at least one inflexible prevascularized constructs with an engineered tissue, before or after the tissue is implanted in a human patient. The skilled artisan will also appreciate that these techniques may be used with any engineered tissue to produce a vascularized engineered tissue.

Although the invention has been described with reference to various applications, methods, and compositions, it will be appreciated that various changes and modifications may be made without departing from the invention. The foregoing examples are provided to better illustrate the invention and are not intended to limit the scope of the invention.

What is claimed is:

1. A method for vascularizing an engineered tissue in a subject, comprising:
    a. combining at least one prevascularized construct with said engineered tissue, wherein said construct contains freshly isolated autologous microvessel fragments in a biocompatible three-dimensional culture matrix; and
    b. implanting said engineered tissue, thereby vascularizing said engineered tissue in vivo.

2. The method of claim 1, wherein said combining comprises attaching at least one prevascularized construct to said engineered tissue.

3. The method of claim 2, wherein said attaching comprises suturing, stapling, gluing, or combinations thereof.

4. The method of claim 1, wherein said at least one prevasctilarized construct comprises at least one microvessel fragment obtained from a vascular tissue.

5. The method of claim 4, wherein said vascular tissue is skin, skeletal muscle, cardiac muscle, atrial appendage of the heart, lung, mesentery, or adipose tissue.

6. The method of claim 1, wherein said engineered tissue is selected from the group consisting of heart tissue, lung tissue, cardiac muscle tissue, striated muscle tissue, liver tissue, pancreatic tissue, cartilage, bone, pericardium, peritoneum, kidney, smooth muscle, skin, mucosal tissue, small intestine, and large intestine.

7. The method of claim 4, wherein said at least one microvessel fragment is obtained from a human.

* * * * *